United States Patent [19]
Smyth

[11] Patent Number: 6,120,461
[45] Date of Patent: Sep. 19, 2000

[54] APPARATUS FOR TRACKING THE HUMAN EYE WITH A RETINAL SCANNING DISPLAY, AND METHOD THEREOF

[75] Inventor: Christopher C. Smyth, Fallston, Md.

[73] Assignee: The United States of America as represented by the Secretary of the Army, Washington, D.C.

[21] Appl. No.: 09/371,706

[22] Filed: Aug. 9, 1999

[51] Int. Cl.[7] .................................................. A61B 5/00
[52] U.S. Cl. ............................................ 600/558; 351/209
[58] Field of Search ............................ 600/558; 351/209, 351/210

[56] References Cited

U.S. PATENT DOCUMENTS

| | | | |
|---|---|---|---|
| 3,628,193 | 12/1971 | Collins | 600/558 |
| 3,766,311 | 10/1973 | Boll | 600/558 |
| 5,410,376 | 4/1995 | Cornsweet et al. | 351/210 |
| 5,583,795 | 12/1996 | Smyth | 364/516.444 |
| 5,649,061 | 7/1997 | Smyth | 395/20 |
| 5,895,415 | 4/1999 | Chow et al. | 607/54 |

Primary Examiner—Cary O'Connor
Assistant Examiner—Pamela L. Wingood
Attorney, Agent, or Firm—Paul S. Clohan, Jr.

[57] ABSTRACT

A retinal scanning display, an active-pixel image sensor array, and an image processor track the movements of the human eye. The scanning nature of the display acts as a sequential source of eye illumination. The active-pixel image sensor array is directed toward the cornea of the eye through a matrix of micro-lens. The sensor is integrated with a comparator array which is interfaced to bilateral switches. An element address encoder and latch determines the sensor element which reaches maximum intensity during the raster-scan period of the display driver. Over a display field refresh cycle, the invention maps the corneal surface to a data table by pairing sensor activations to the specular reflections from the cornea of the sequenced source lights.

9 Claims, 16 Drawing Sheets

APPARATUS FOR TRACKING THE HUMAN EYE WITH A RETINAL SCANNING DISPLAY, AND METHOD THEREOF

RIGHTS OF THE GOVERNMENT

The invention described herein may be manufactured, used, and licensed by or for the United States Government for governmental purposes without the payment to us of any royalty thereon.

BACKGROUND OF THE INVENTION

1. Field of the Invention

The invention is a form of oculometer and as such may be used to measure the eye gaze direction and fixation duration, as well as the dual eye binocular convergence point. The invention has potential applications to the medical, scientific, engineering, manufacturing, military, and entertainment domains.

As examples, the invention may be used as a tool for the medical diagnosis of ocular functions, as an aid to the paraplegic handicapped, for the measurement of ocular functions and workload in human factors studies, as a measure of subject training, as a tool for fatigue monitoring, as part of an electronic safety net to detect performance degradation due to pilot incapacitation in piloted and tele-operated vehicles, as a component of an electronic intelligent pilot-vehicle interface used for adaptive aiding in piloted and teleoperated vehicles, for task scan analysis including measuring situation-awareness, for human operator control of machines and interaction with computer games, and for advertisement and usability analysis.

The invention is designed to be used with head-mounted video displays such as those that have been developed for virtual reality, stereographic displays, monocular or binocular vision helmet mounted displays, and night vision goggles. These displays are used in piloted helicopters, vehicles, and control stations for teleoperated robotics. The invention can be used as an eyetracker to control computerized machines from an electronic video display by the ocular gaze point of regard and fixation duration.

2. Discussion of Related Art

The present invention relates to U.S. Pat. No. 5,583,795, with the further improvements of: (1) a retinal scanning display as a light source, (2) a semiconductor, active-pixel image sensor array with integrated circuits for activating a charge coupled device (CCD) array, or in a further embodiment, a random access memory cache, to acquire an image of the human eye, and (3) expansion of the image processing to include inner structures of the eye and the retinal return.

The existing technology for oculometers is based upon the optical measurement of reflected infrared light from the human eye, and is more than forty years old in concept. In its present form, an oculometer contains a single infrared light source which is directed at the eye, and the reflected light is imaged onto a charge-coupled device (CCD) sensor array. The image of the eye is then electronically processed to determine the corneal reflection point and the pupil centroid. These parameters are used to determine the angular location of the eye relative to the camera within a fair degree of accuracy. The technology is either head-mounted or mounted in a panel in front of the user.

U.S. Pat. No. 5,583,795, referred to above, using a video display and an optical transistor sensor array, was an improvement in the existing technology. The video display is treated as a sequential array of light sources. The sensor array is integrated to a comparator array and an address encoder and latch, with both circuits clocked by the raster scan pulse of the display driver. This design is used to construct a data table pairing the sensors activated by specular reflections from the cornea to the sources as they are sequenced over the display field refresh cycle. Using ophthalmometric techniques, a three dimensional model of the external surface of the cornea is computed from the pairing table. The optical axis and the corresponding viewing direction are then computed from the model. In a further embodiment, the pupil center is located for computing the optical axis. This is done with ray tracing using the positions of the source and sensor paired by the reflection point located at the pupil centroid. Here, the centroid is determined from an image of the eye collected over the display field refresh cycle by a charge coupled device (CCD) array operating in parallel with the sensor array.

In this continuation of that patent, a retinal scanning display replaces the video display as a sequential source of light. In a further development, an improvement to the design of the sensor array is described for activating a CCD array, or in a further embodiment, a random access memory cache, to acquire an image of the eye. In a still further development, the optical-transistor sensor array and supporting circuits is embodied as an active-pixel image sensor array with integrated circuits, made from a complementary metal oxide semiconductor (CMOS). Finally, the image processing is expanded to include the inner structures of the human eye such as the pupil and iris, and the retinal return from the fundus.

Advantages Over Prior Art:

The light sources for the invention are produced by a retinal scanning display used as an imaging system in which the directed light sweeps the retina of the human eye for display effects. In this imaging system a modulated, coherent light sequentially illuminates adjacent point-wise portions of the human retina. The invention makes use of the shift in illumination of the human eye that occurs as the directed light scans in an orderly sequence.

The advantage of the retinal scanning display is that the eye is illuminated in exact, discrete steps. This generates a succession of precise reflection points from the cornea of the eye for processing by the sensor array of the invention. This is in comparison to the phosphorous video displays used in related U.S. Pat. No. 5,583,795 where successive elements of the display remain illuminated for a short time following activation resulting in relatively blurred reflection points.

Furthermore, the illumination from the retinal scanning display is brighter and more intense than that produced by the phosphorous video displays. This results in a more definite image of the pupil and an image return from the inner structures of the eye including the retina.

The invention uses an active-pixel image sensor array on a complementary, metal-oxide semiconductor (CMOS) substrate with integrated circuits in a parallel point array architecture. The design is readily manufactured as a very large scale integrated (VLSI) circuit array chip made from CMOS field-effect transistors (FET). The large scale of the design provides a resolution that is fine enough for accurate mapping of the cornea, and an image of the eye suitable for image processing. Furthermore, the CMOS VLSI array can perform at megahertz rates due to the circuit architecture. This is necessary for processing images at the raster-scan illumination rates of the retinal scanning display.

The point array architecture is a unique circuit design which ensures a highly accurate three dimensional mapping of the cornea. The point array circuit is a photo-diode, transistor integrated with a specular-threshold comparator and a bilateral switch. The switch performs as an element of a "winner-take-all" array for an encoder and latch circuit. The circuit is clocked by the raster-scan pulse of the display driver and determines the sensor element with maximum intensity above the specular threshold. A digital processor accesses the latched encoder to construct a corneal mapping table which pairs the directed light to the sensors activated by specular reflections from the cornea. This occurs as the directed light is sequenced over the display field refresh cycle.

The point array architecture employs novel circuits to acquire an image of the eye in a CCD array from diffused reflection without washout. This is necessary since the accumulation of specular reflections over a display refresh cycle would washout the image. At each raster-scan pulse, the outputs of all sensor array elements with intensities less than that for specular reflection are passed pixel-wise to the CCD. The output of each such element, as determined by a point-array specular-threshold comparator, drives a light-emitting-diode matched to a CCD array element through a bilateral switch. This is an improvement to a prior invention which provided no threshold limit.

In another embodiment, the sensor array acquires an image of the eye in a random-access-memory (RAM) cache. This embodiment, integrated with multiple memory caches, supports faster image processing. The outputs of the sensor-pixel elements drive point-array analog-to-digital converters. These output in turn to digital circuits for reading, adding, and writing to the RAM cache. Here, one cache can be downloaded while another is being loaded during a display field refresh cycle. The processing rate of a CCD array is limited by the bucket-brigade technique of downloading array values.

The invention employs a unique CMOS design which rapidly process the image acquired in the CCD array or RAM cache, at each display field refresh pulse. The image processor is embodied as a stack of very-large-scale integrated (VLSI) circuit arrays, which controlled by a central processing unit (CPU) is operated en masse along matched array elements. The stack design supports the application of advanced image processing techniques to isolate and enhance portions of the image, and to abstract the image coordinates of key features. These include the location and principal axes of the pupil centroid, and the image coordinates of the cluster points of the retinal capillary network following isolation from the retinal return. In addition, the image coordinates of key features of the inner structure of the human eye are computed such as the sphincteral pattern of the iris. The determination of these features provides the basis for a real-time three dimensional modeling of the human eye at the display field refresh rate.

The invention uses a novel method to compute the locations of features within the human eye from the corneal mapping table and the image coordinates accumulated over the display refresh cycle. The features are used to determine a three dimensional model of the human eye. In this method, an accurate model of the cornea is first computed from the listing of sensors to directed source lights paired by the digital processor. This model is used to locate the corneal center and the major and minor axes. With the corneal model, the method next computes the intraocular locations of features that are part of the inner structure of the human eye. This is done by first finding corneal reflection points which listed in the table are located at or near an image feature, interpolating a corneal surface refraction point, and then tracing an ophthalmic ray from that point back to the feature in the eye. This novel ophthalmomatric ray tracing method makes use of the corneal mapping to produce the optical locations within the eye of the key features isolated by the image processor.

The invention uses a best fit to a three dimensional model of the eye to compute the optical origin and the optical and median axes from the values for the corneal and internal features. These include the corneal optical center, the corneal surface center and axes, the pupil optical center, the pupil orientation, the capillary network of the retinal fundus, and the sphincteral pattern of the iris. Finally, the invention computes the viewing origin and axis for the eye from the optical origin and axis, and the median axes. The invention then locates the viewing origin and axis in the coordinate system of the retinal scanning display. The invention measures the visual gaze direction, point of regard, and the fixational duration from the location of the display in the workplace.

The invention is easily extended to the simultaneous tracking of both eyes allowing the measurement of the optical convergence point in the users three dimensional workspace either real or virtual.

The invention is auto-calibrating since the user can quickly and accurately go through a calibration procedure that correlates visual fixation position with line of sight.

The accuracy of the invention is independent of shifts of the helmet holding the display on the user's head; the shifts are caused by changes in facial-expression and head movement dynamics. This is due to the ability to compute an exact eye model from the locations of the light source and the sensors which are fixed by the helmet-construction. Measurements of the helmet location and orientation are used to relate the visual axes to the user's three dimensional workspace.

SUMMARY OF THE INVENTION

Accordingly, it is an object of the present invention to provide an apparatus for tracking the human eye with a retinal scanning display.

The foregoing and other objects are achieved by an invention that uses a retinal scanning display, an active-pixel image sensor array with integrated circuits, and an image processor to track the movements of the human eye. The scanning nature of the display acts as a sequential source of eye illumination; the display may be task related or a near-infrared light used to track the eye. The active-pixel image sensor array, embodied as a complementary metal oxide semiconductor (CMOS) substrate, is directed toward the cornea of the eye through a matrix of micro-lens. The sensor is integrated with a comparator array which is interfaced to bilateral switches. An element address encoder and latch determines the sensor element which reaches maximum intensity during the raster-scan period of the display driver. Over a display field refresh cycle, the invention maps the corneal surface to a data table by pairing sensor activations to the specular reflections from the cornea of the sequenced source lights.

Furthermore, at each raster-scan pulse, the electronics accumulate pixel-wise the intensities of the sensor elements to activate a charge-coupled device (CCD) array for acquiring an image of the eye from the diffused reflections. This is done for those sensor-pixel elements which have intensities that are less than that for specular reflection, as determined by an array of limit comparators. The comparators control an array of transistor-driven emitters which are mapped one-to-one to the CCD array through an array of one-of-two switches. The intensity limiting precludes specular wash-out of the image. In another embodiment, a memory cache replaces the CCD array, and the emitters are replaced by analog-to-digital converters in series with digital read-adder-write circuits.

The invention computes at the display field refresh cycle pulse, a three dimensional model of the eye from the source to sensor pairing table and the eye's image. First, the image processor, embodied as a stack of very-large scale-integrated (VLSI) circuit arrays, isolates features for the pupil, retinal fundus, and iris. The invention next computes a three-dimensional model of the cornea by applying an ophthalmometric ray tracing technique to the pairing table. The invention then computes optical locations for the isolated image features with the ophthalmomatric ray tracing and the corresponding image locations and the pairing table.

Using a best fit to a three dimensional model of the eye, the invention computes the optical origin and the optical and median axes from the values for the cornea and internal features. These include the corneal optic center, the corneal surface center and axes, the pupil optic center, the pupil image orientation, the capillary network of the retinal fundus, and the sphincteral pattern of the iris. Finally, the invention computes the viewing origin and axis for the eye from the optical origin and axis, and the median axes. The invention may be used to measure visual gaze direction, point of regard, and the fixational duration.

BRIEF DESCRIPTION OF THE DRAWINGS

The invention will be better understood, and further objects, features, and advantages thereof will become more apparent from the following description of the preferred embodiment, taken in conjunction with the accompanying drawings in which.

DETAILED DESCRIPTION OF THE PREFERRED EMBODIMENTS

Figure 1:
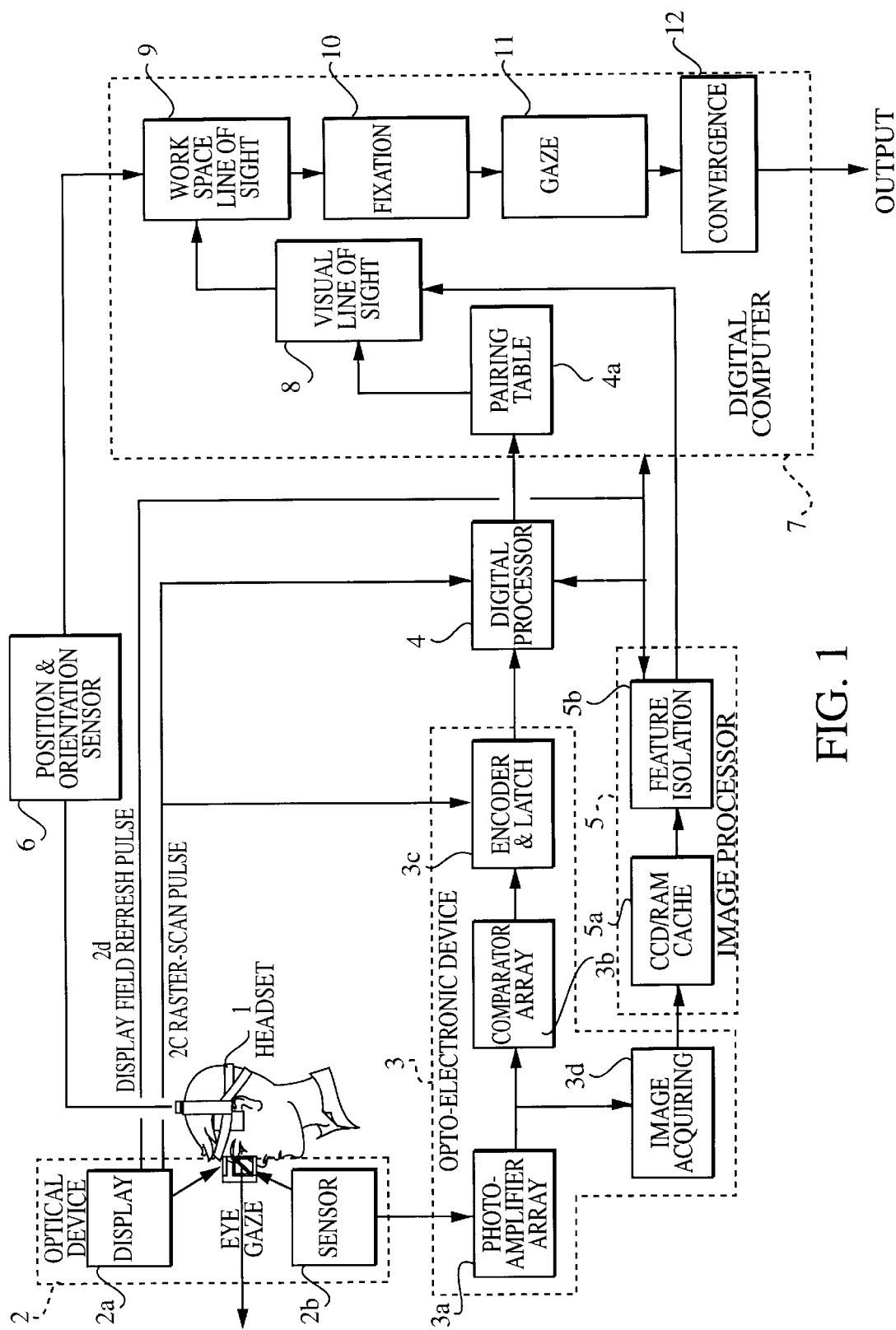
FIG. 1 is a schematic of the electronic hardware and software components of the invention.

As shown in FIG. 1, the invention consists of an optical device 2 mounted on a headset 1, an opto-electronic device 3, a digital processor 4, an image processor 5, a headtracker 6, and a digital computer 7. The video device 2 contains an imaging display 2a and a sensor system 2b. The imaging display 2a illuminates the user's eye; the sensor system 2b detects the reflections from the eye of the illuminating source. The optical output of the sensor system 2b is the input to the photo-amplifier array 3a of the opto-electronic device 3. The electrical output of the array 3a is the input to the comparator array 3b which in turn provides electrical input to the encoder and latch 3c. The electrical output of the encoder and latch 3c is the electrical input to the digital processor 4. The comparator array 3b isolates the amplifier element of the array 3a which first responds to the illuminating element of the imaging display 2a. The processor 4 writes the corresponding encoded address from the latch 3c to a double buffered digital memory 4a, on the clocked raster-scan pulse 2c from the imaging display 2a. The digital memory 4a is shared with the digital computer 7.

The electrical output of the array 3a is also inputted to the image-acquiring array 3d which in turn inputs to the CCD array 5a of the image processor 5. In a further embodiment, the CCD array 5a is replaced by a random-access memory (RAM) cache. The pupil centroid and other image features of the eye are isolated by processor 5b upon receipt of the clocked display-field refresh pulse 2d from the imaging display 2a. The electrical output of processor 5b is digital input to the digital computer 7. In a further embodiment, the image of the inner structures of the eye including the retinal capillary network and the sphincteral pattern of the iris, is quantified and inputted to the computer. The digital computer runs several processes which are released from hibernation upon receipt of the clocked display-field refresh pulse 2d from the imaging display 2a. These are routines to compute: the visual line of sight 8, the workspace line of sight 9, fixations 10, gaze points 11, and finally the binocular convergence point 12 for the dual eye system.

The invention uses the video imaging display 2a to illuminate the eye in a rapid and controlled manner. The imaging system is a form of retinal scanning display in which directed light sweeps the retina of the human eye for display effects. The sequence of momentary shifts in light direction generated during the electronic refresh-sweep of the display, provides an accurate and rapid sequence of point light sources. The invention makes use of the shift in illumination of the human eye that occurs as the display is scanned in an orderly sequence. The scanning pattern generates a momentary shift in brightness during the electronic refresh of the display. This momentary flare in brightness is detected by electronic sensors; however, it is not noticed by the human eye which averages out transients in brightness less than 0.10 seconds. This use of the video imaging system for light sources reduces the components needed for eye-tracking.

In one embodiment, the imaging system is a low-energy laser diode which directs a modulated, coherent light sequentially so as to point-wise illuminate adjacent portions of the human retina. The system may use a raster method of image scanning to drive the laser with video sources. Here, a horizontal scanner moves the laser beam to draw a raster row of pixels; a vertical scanner then moves the laser to the start of the next line. In this manner, the spectrum of a colored-light laser used for display generation, is used for eye-tracking following filtering of the reflected light. In another embodiment, a near-infrared, low-energy laser diode with light invisible to the human eye, may be moved in a sequentially scanning pattern as an illuminating source for eye-tracking alone.

Figure 2:
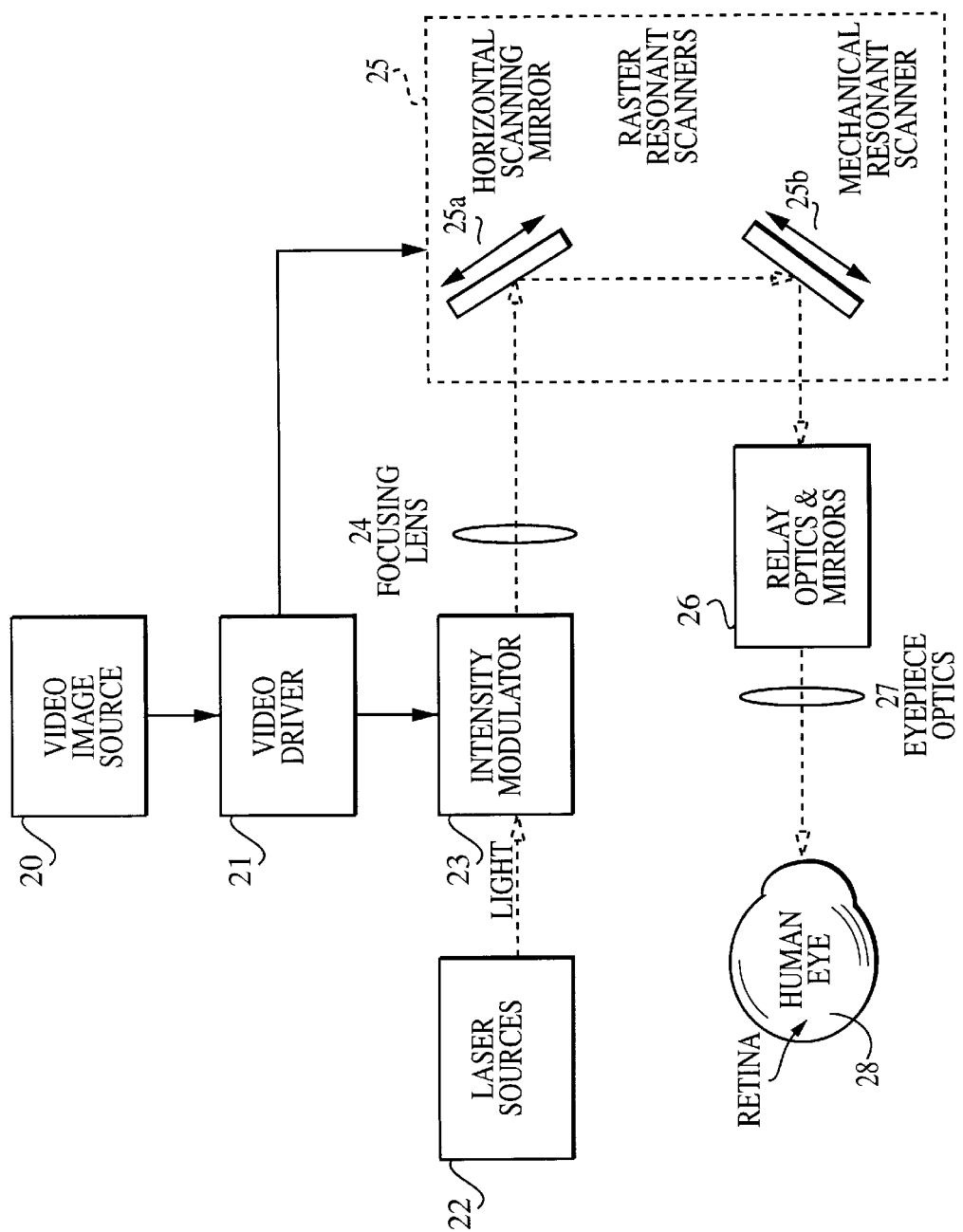
FIG. 2 is a schematic of a retinal scanning display for the invention.

FIG. 2 shows a schematic of a laser-driven retinal scanning display system. The video image source 20 is the input to an electronic video-driver 21. The driver controls an intensity modulator 23 and the raster resonant scanners 25 consisting of a pair of high-speed scanning mirrors. The output of the laser 22, modulated for intensity by 23, is focused on the scanners 25 by the achromatic lens 24. The light from the scanners is redirected by the relay optics and mirrors 26 to the retina 28 of the human eye, through the eye-piece optics 27. The laser 22 generates a low-energy, coherent, pin-point beam of light which produces a diffraction limited spot on the retina. The video-driver 21 synchronize the scanners and intensity modulator with the incoming video signal.

The driver 21 electronically decodes and combines text, graphics and video input 20 into an image and then divides the resulting image into patterns of individual pixels. The intensity modulator 23 digitally modulates the stream of laser light to recreate the intensity of each individual pixel. The outputs from three different colored-light lasers can be combined and synchronized for partial or full-color. The light modulation is synchronized by the video-driver with the high-speed scanning mirrors to locate each image pixel. One mirror 25a provides the horizontal location of the beam, while the other 25b provides the vertical scan. The mirrors rapidly move the beam horizontally from pixel to pixel and vertically line to line to make an image. Existing prototypes such that developed by Micro Vision of Seattle, have a pixel refresh rate of 18.432 million times per second thereby producing a 640×480-pixel virtual image 60 times a second.

Figure 3:
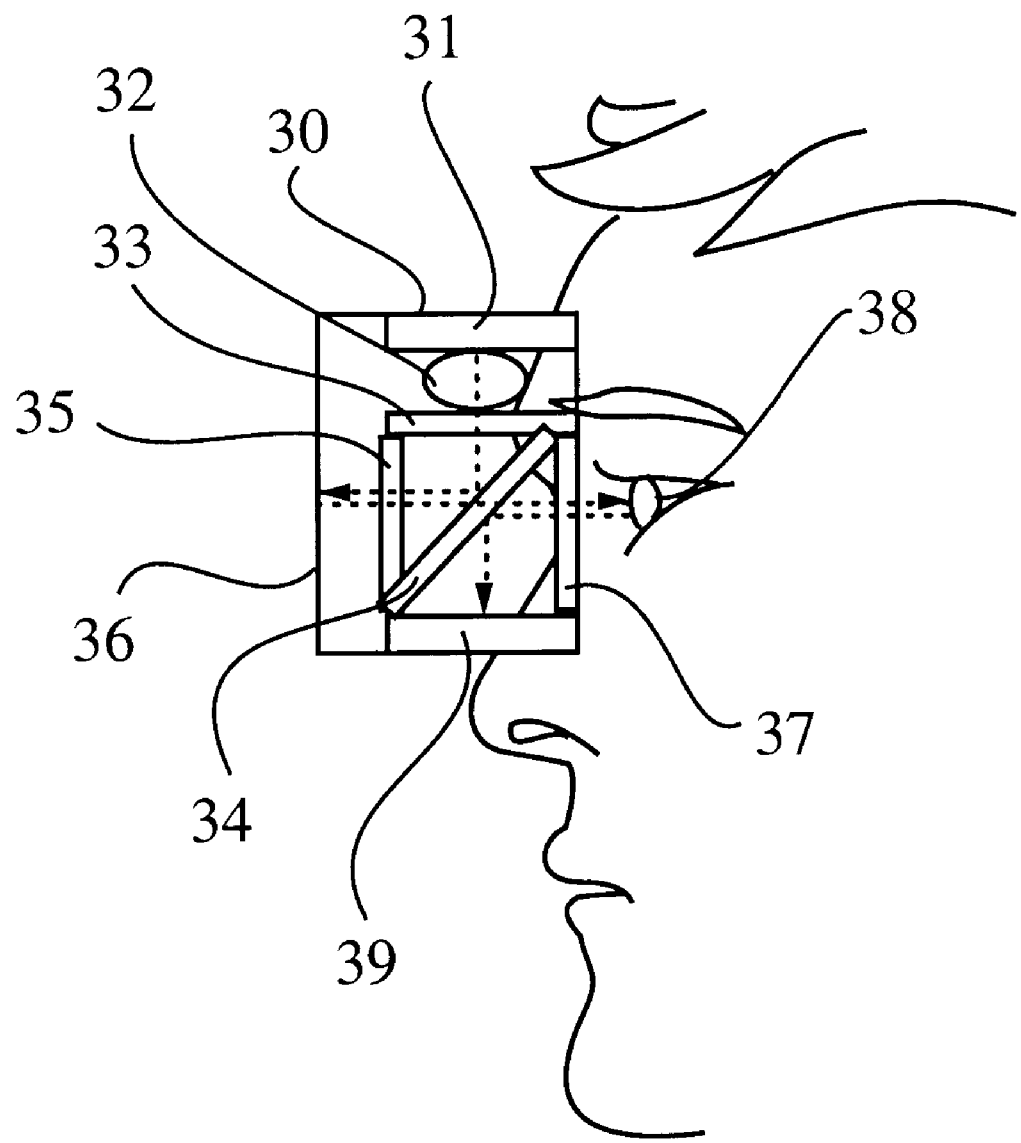
FIG. 3 is a drawing of a headset-mounted optical device which contains the retinal scanning display and the active-pixel sensor array.

The optical device 2 may be incorporated into a head mounted display system 30 as shown in FIG. 3. Here, the user is wearing a head-mounted retinal scanning display 31 (with eyepiece optics 32) making up display 2a, and a periocular array 39 of light sensors 2b, all packaged as a complete unit 30 with display optics. The display image light from 31 reflected from the user's eye is directed back to the periocular array of light sensors 39 by the display optics. The geometrical design of the display optics is determined by the locations of the display 31 and the sensor array 39 relative to that of the viewer's eye. The virtual display design shown in FIG. 3 employs an on-axis folded optical geometry.

In this case, the light from the imaging display 31 is focused by the eyepiece lens 32 through a dielectric linear polarizer 33 and folded by a mirror/splitter 34 in the form of a linear polarizer with the plane of polarization rotated 90 degrees. The light then passes through a quarter-wave rotator (wave plate) 35 to the front visor/combiner 36. The light reflected from the visor 36 passes back through the wave plate 35 and with the light now rotated 90-degrees, passes back through the mirror/splitter 34, from which it passes through another quarter-wave plate 37 to the eye 38. The light reflected from the eye 38 passes back through the wave plate 37, and with the light rotated another 90 degrees, is folded by the mirror/splitter 34 onto the periocular array 39 of electronic light sensors 2b. The array of electronic light sensors 2b detects the display generated light reflected back from the cornea and internal components of the eye such as the iris surrounding the pupil and the fundus of the retina. Of course, other designs are possible for the optical device where similar comments apply to the optical geometry. In all designs, the light reflected from the eye 38 passes back through the wave plate 37, and is folded by the mirror/splitter 34 onto the periocular array 39 of electronic light sensors 2b.

Figure 4:
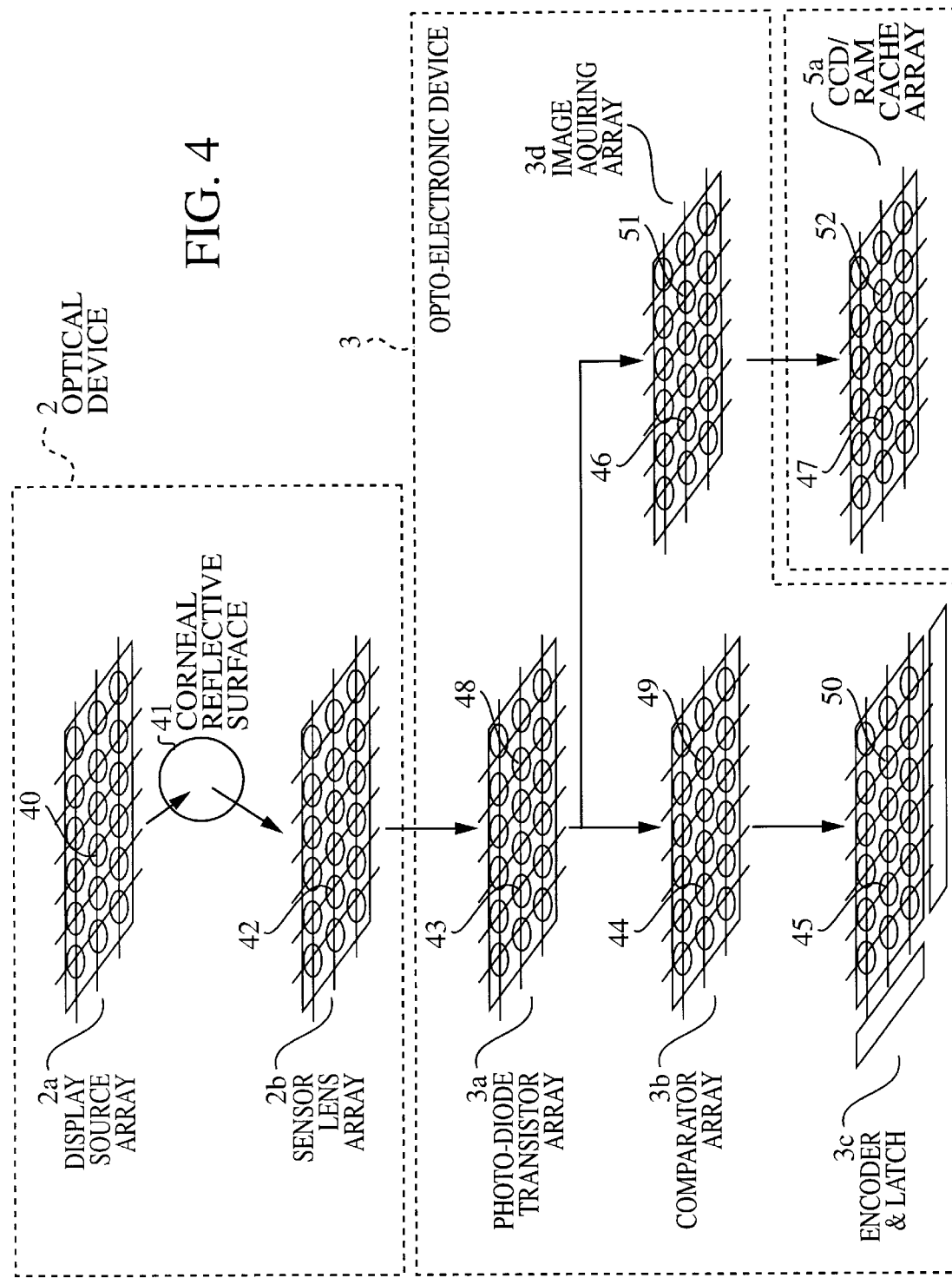
FIG. 4 is schematic showing the processing layers of the active-pixel sensor array.

The light sensor array 2b may be a set of micro-lens interfaced to a fiber-optics bundle probe. FIG. 4 shows the output of the optics probe feeding a two-dimensional array of photo-transistors 3a (or photo-diode, transistor amplifier elements). A spectral filter (not shown) is used to ensure that light with a wavelength of the center value for the quarter-wave plate 37 is collected for eye-tracking and not extraneous display light or ambient light from the surround.

The array of photo-transistors 3a converts the light reflected from the eye to an electrical current distribution matching the image. As shown in FIG. 4, the opto-electronic device 3 consists of layers of arrays matched across corresponding pixel elements with the photo-detector array 3a receiving the incident light. The sets of matched elements function as parallel processing channels with two outputs for each channel. One output is to the digital processor 4 through the encoder and latch 3c for determining the point of specular reflection on the cornea. The other output is to the image processor 5 through the CCD 5a for processing the diffused reflections from the surfaces of the eye.

FIG. 4 shows the outputs of the photo-detector array 3a being piped one-to-one to an array of comparators 3b where the amplified output of each photodetector of 3a is compared to a threshold level for specular reflection. The threshold level is set to collect the brightest part of the image. The level is set above the system noise which is mainly due to optical reflections from the other sources, the photo-transistor dark noise, and the Schottky, Johnson, and flicker noises in the amplifiers. The comparator array 3b is interfaced to a matrix array static encoder 3c. A comparator voltage output above the threshold level forces the corresponding matrix address on the output lines of the encoder 3c. The encoder output code is latched for the remaining duration of the raster-scan clock cycle period. The circuit 3c is clocked by the raster-scan pulse of the display driver, and determines the sensor element with maximum intensity. The first switch to close during a raster-scan cycle, causes the latch to be set with the matrix address of that switch. The latch is reset by the next raster-scan pulse.

The outputs of the photo-detector array 3a are also piped one-to-one to the elements of the image acquiring array, 3d. This array acquires an image of the eye in a CCD array 5a by preventing specular-reflective "washout", over a display refresh cycle. At each raster-scan pulse, the output intensities of the photo-detector elements are passed pixel-wise to the CCD. This is done for all elements with intensities less than that of the specular threshold. This point-array configuration accumulates an image of the eye from diffused surface reflections, over the display-field refresh cycle. The image is downloaded from the CCD array to the image processor 5b at the display-field refresh pulse, 2d.

At any moment during a raster-scan clock cycle, the eye is illuminated by a single source light, say 40 of the display, 2a. The incident light is specularly reflected from the anterior surface of the cornea to create a virtual image of the source. The corneal reflex 41 has a bell-shaped light distribution with the brightest part at the center of the image corresponding to the reflection point. The photo-transistors 3a detect the corneal reflex (first Purkinje image) of the light source from the outer surface of the cornea. Here, the photo-transistor element, say 43 is receiving light collected from the brightest point 41 by the micro-lens 42 and is the first to generate maximum current. This follows activation of the source 40 at the start of the raster-scan clock cycle.

FIG. 4 shows the elements 43, 44, and 45 of opto-electronic device 3 constituting one processing channel that is matched to the micro-lens 42, while 43, 46 and 47 make up the other channel. Here, the output of photo-detector element 43 responding to the brightest portion of the specular reflection, causes the matched comparator 44 to reach the threshold first during the clock cycle. This in turn, forces the encoder output to be latched to the address of that comparator element through the switch 45. In this way the electronic encoder 3c isolates the photo-transistor 43 of 3a with maximum response to the corneal reflex 41 from the instantaneously excited light source 40 of the display, 2a.

The CCD array element 47 receives no light from the matched image acquiring element 46, during the raster scan clock cycle. This is because the intensity output of the corresponding photo-detector 43 exceeds the specular threshold as determined by the matched comparator 44. In contrast, the output of photo-detector element 48, with an intensity less than that of the specular threshold as determined by the comparator 49 in the corresponding processing channel, drives a light-emitter 51 matched to a CCD array element 52, while leaving the array switch element 50 unlatched.

The electrical output of the latched encoder 3c is the electrical input to the digital processor 4 and on the raster scan clock pulse 2c the processor 4 writes the encoded address from the latch 3c for the photo-detector 43 to a double buffered digital memory 4a shared with the digital computer 7. The encoder latch is reset by the raster scan clock pulse 2c; the reset is momentarily delayed to allow interaction with digital processor 4. The vertical and horizontal matrix address of the corresponding display source element 40 is determined by the display refresh order, which is indexed by the raster scan clock pulse count. The process is repeated by processor 4 during the display refresh cycle, producing a digital memory table 4a of array matrix addresses for phototransistor sensor 2b and light source 2a pairings, which is accessible by the digital computer 7 routines. The digital memory 4a is buffered and the raster scan clock pulse counter is reset to zero on the clocked field refresh pulse 2d.

Figure 5:
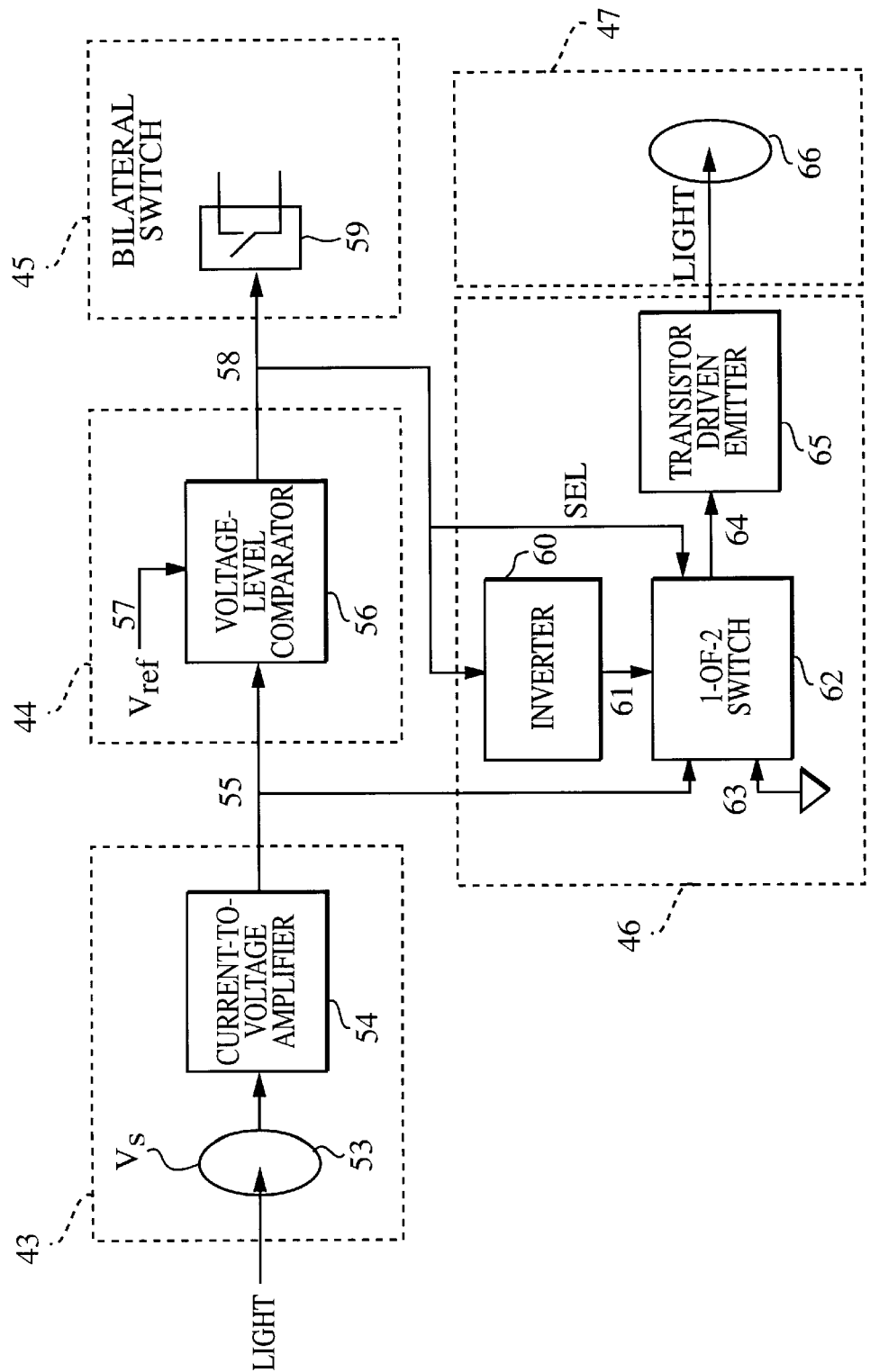
FIG. 5 is a schematic of the conventional architecture for an array point of the active-pixel sensor.

FIG. 5 shows a conventional electronic component architecture for a point array processing channel of the opto-electronic device 3. The light collected by the sensor 2b element of the channel is transformed by the photo-diode 53 into a current, and that in turn to a signal voltage 55 by a current-to-voltage transistor amplifier 54. Here, both components comprise the channel element of the photo-detector array 3a, say element 43. The signal voltage 55 is input to a voltage level-comparator 56, which as part of the comparator array 3b element 44, outputs a selector voltage 58, when the signal voltage exceeds the specular threshold 57. The selector voltage controls a bilateral switch 59, which closes when the signal voltage exceeds the specular threshold. The switch is the "winner-take-all" element 45 of the encoder and latch 3c.

The selector signal 58 from the voltage level-comparator 56, is inverted by the inverter 60 to control a 1-of-2 switch 62. The switch has inputs from the signal 55 and ground 63, and output 64 to a transistor driven, light-emitter 65. The inverter 60, switch 62, and emitter 65 together comprise the point-array channel element 46 for the image acquiring layer 3d, with light output to 66 of the CCD array element 47 when the signal 55 is less than the specular threshold 57.

In a further embodiment, the opto-electronic device 3 is an active-pixel array on a complementary metal-oxide semiconductor (CMOS) substrate, with integrated circuits. The CMOS design is a very-large-scale-integrated (VLSI) circuit with parallel point array architecture. The point array is made up of CMOS field-effect transistors (FET) performing functions equivalent to those of the conventional element architecture described above. The advantage of the CMOS VLSI array design over the conventional architecture is: (1) the small chip size for the large array needed for fine image resolution, and (2) the ability to perform at the megahertz raster-scan rates of retinal scanning displays, due to the parallel point-array circuit architecture.

Figure 6:
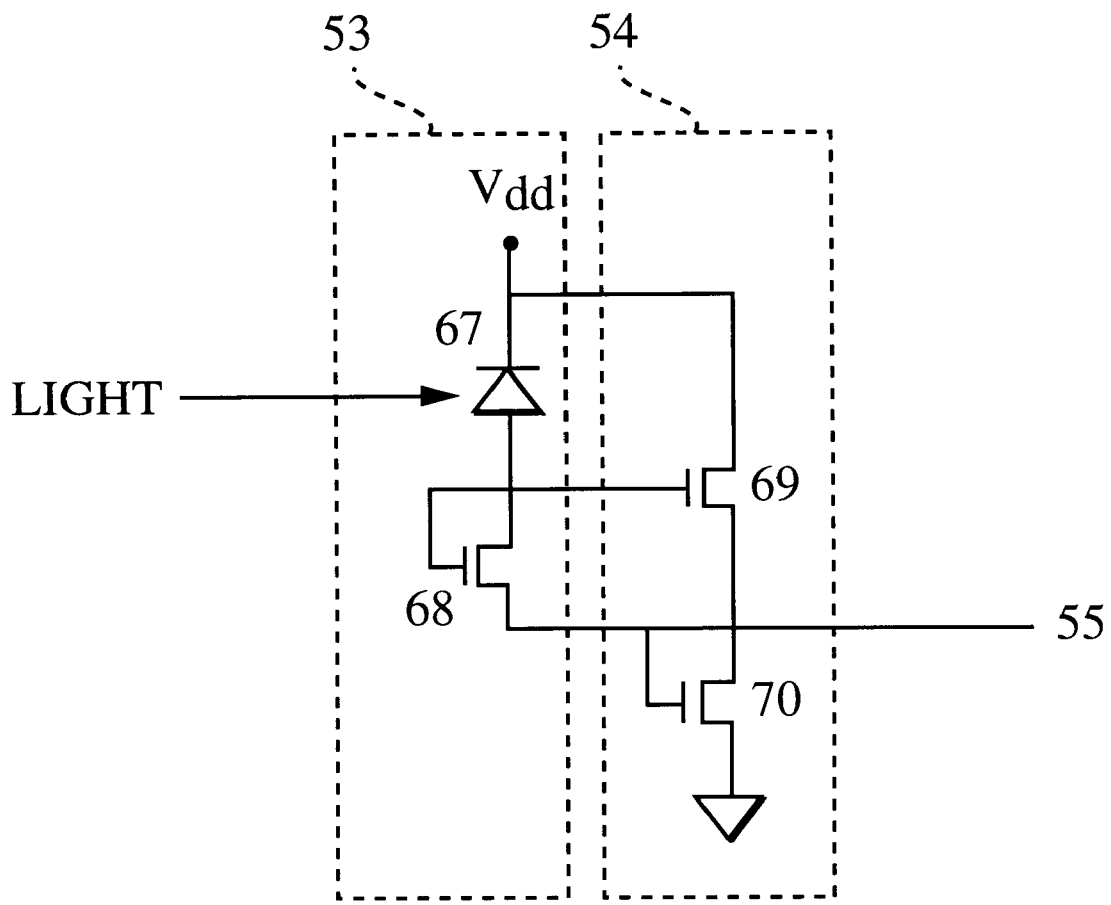
FIG. 6 is a schematic of a CMOS FET architecture for the photo-diode transistor amplifier element of an array pixel.
Figure 7:
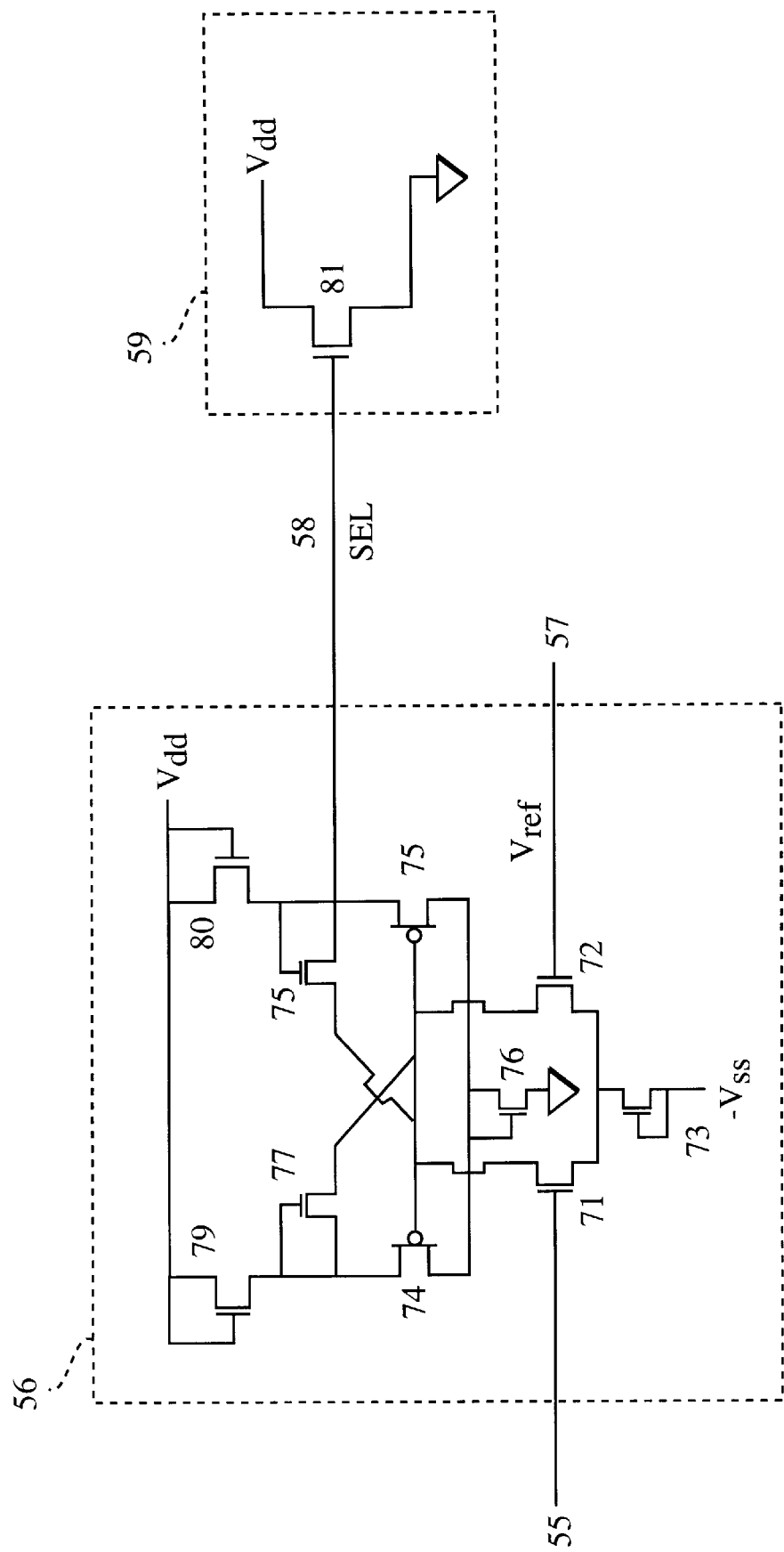
FIG. 7 is a schematic of a CMOS FET architecture for the voltage comparator and bilateral switch elements of an array pixel.
Figure 8:
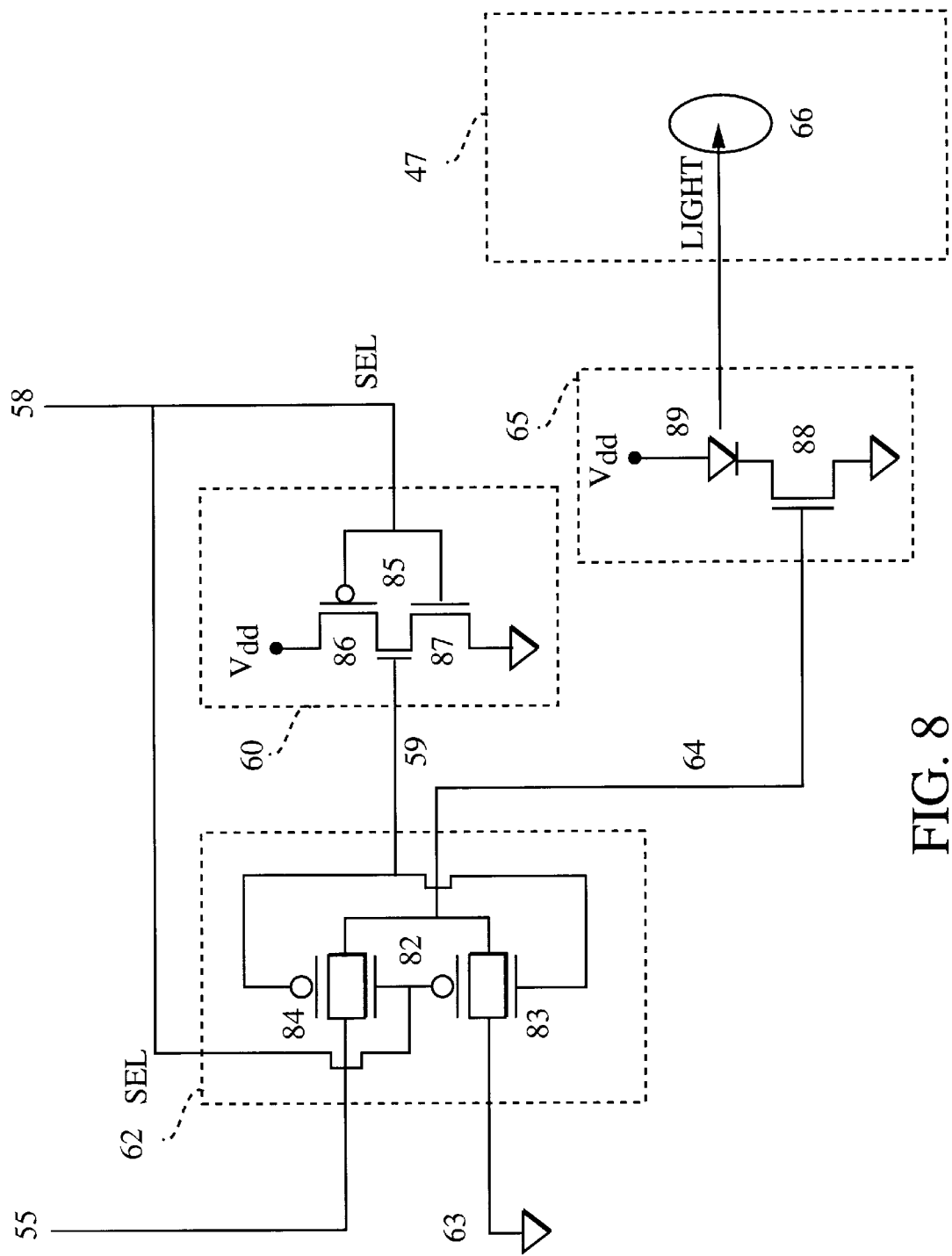
FIG. 8 is a schematic of a CMOS FET architecture for the image acquiring element of an array pixel used for accumulating a CCD image.

FIGS. 6 through 8 show equivalent CMOS FET designs for the elements of the opto-electronic device 3. FIG. 6 shows an array point CMOS FET architecture for a photo-diode transistor element comprised of components 53 and 54. Here, the photo-diode 67, back-biased by the supply voltage vdd, produces a light-responsive current through the active resistor load of the enhancement-depletion NMOS FET 68, configured with the drain in feedback to the gate terminal. The voltage across the active resistor controls the gate to source terminal voltage of the NMOS FET 69, and thereby, the current through the active load NMOS FET 70, producing the amplified signal voltage 55.

FIG. 7 shows an array point CMOS FET architecture for the comparator element 56 and the latchable element 59. The comparator element is made up of a difference circuit coupled to a flip-flop. The difference circuit compares the signal voltage 55 to Vref, the threshold reference signal 57. The circuit is composed of the amplifiers NMOS FET 71 and 72, with the NMOS FET 73 as a constant current source with the gate tied to the source terminal, which in turn is biased in the operating range by the negative source voltage, Vss. The flip-flop circuit consists of a pair of PJFET (Junction field-effect-transistors) 74 and 75, cross-coupled by the NMOS FET active resistors 77 and 78, to the supply voltage Vdd, through the NMOS FET active resistors 79 and 80, with a current drain through the NMOS FET active resistor 76. The output of the flip-flop circuit 58, is either ground or supply voltage Vdd, depending on whether the signal voltage is less or more than the reference voltage, 57. This signal is the selector voltage for the bilateral, analog switch 59, composed of the NMOS FET 81. The switch is either open or closed for positive voltages less than the supply, and in this manner is latchable, as a "winner-take-all" element of the encoder and latch circuit 3c.

FIG. 8 shows an array point CMOS FET architecture for the components 60–65 of the image acquiring element. The CMOS FET inverter 85, made up of a PMOS FET 86 and NMOS FET 87 pair in series, provides the inverse selector signal 59 to the CMOS FET "1-of-2" switch 82. The switch is made up of two PMOS FET and NMOS FET pairs 83 and 84 in parallel. The switch output 64 is either the photo-detector output 55 or the ground 63, depending upon the selector voltage 58 and its inverse 59. The output through the gate voltage of the NMOS FET 88, controls the intensity of the light emitted from the light-emitting diode 89 to the CCD array element 66. The LED elements are mapped one-to-one to the elements of the CCD; a relay lens array is inserted between the stages to eliminate the beam spreading caused by diffraction.

Figure 9:
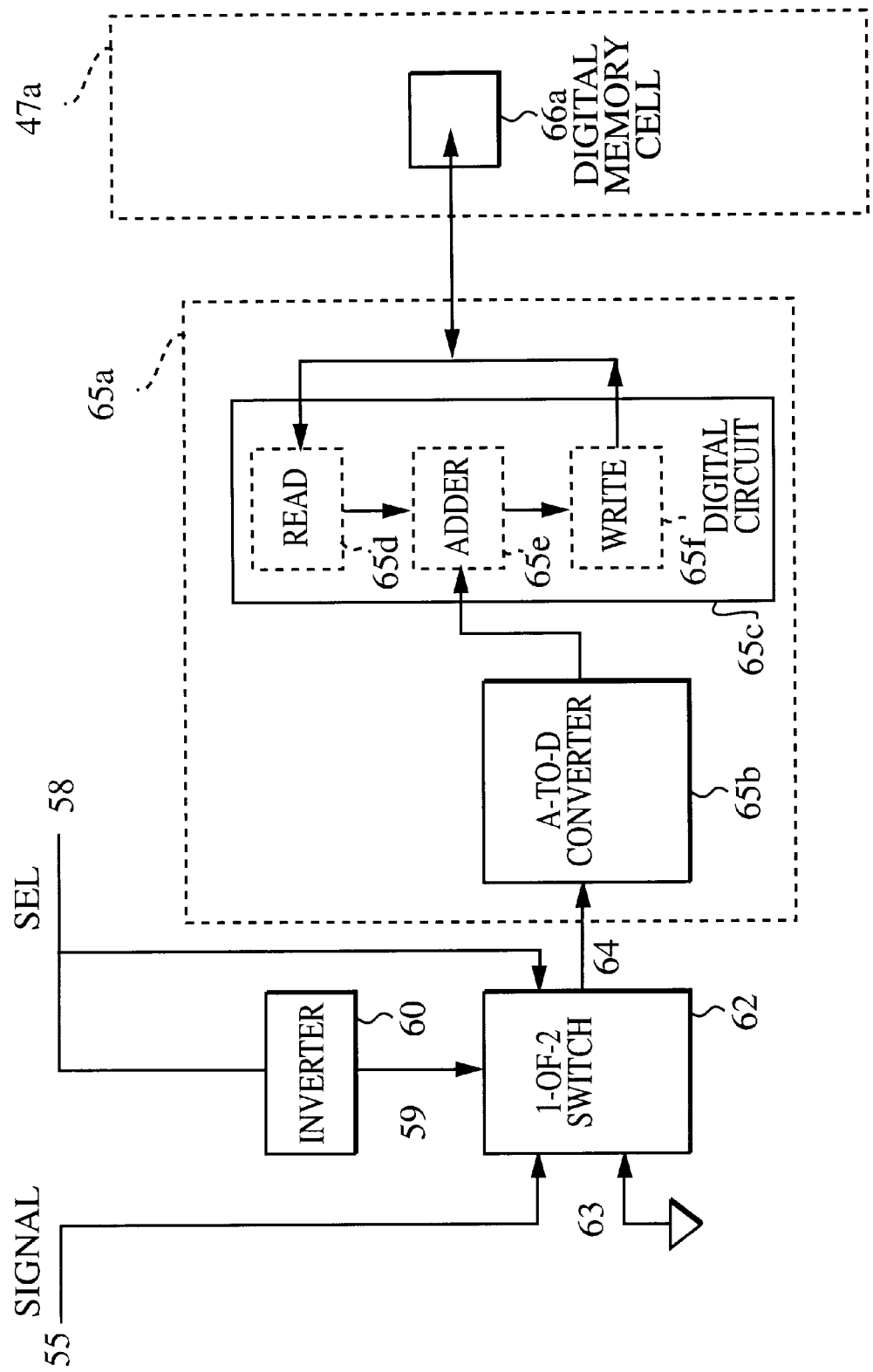
FIG. 9 is a schematic of the architecture for the image acquiring element of an array pixel used for accumulating a memory cache image.

In another embodiment, the array 3d acquires an image of the eye in a random-access-memory (RAM) cache, over a display refresh cycle. FIG. 9 shows modifications to the point-array element of the image-acquiring layer 3d for accumulating an image in a RAM cache. In this embodiment, the emitter 65 is replaced by an element 65a, with an analog-to-digital converter 65b which has a digital output to a digital circuit 65c. The circuit 65c consists of a read-circuit 65d, an adder 65e, and a write-circuit 65f. The read-circuit 65d reads the digital contents of the cache memory location 66a, at the leading edge of the raster scan clock pulse. The adder circuit 65e adds the read value to the digital output of the converter 65b. And, the write circuit 65f writes the digital sum back into the cache memory location. The image in the RAM cache is addressed by the image processor 5b at the display-field refresh pulse. With dual caches, this embodiment has faster processing times than does the CCD array design, which is limited by the bucket-brigade technique. While one cache accumulates an image during a display-field refresh cycle, the other retains the image from the previous cycle for the image processing. The role of the caches are switched at the next refresh pulse. The CMOS FET architecture for analog-to-digital converters and digital circuits are found in the literature and are not described further here.

Figure 10:
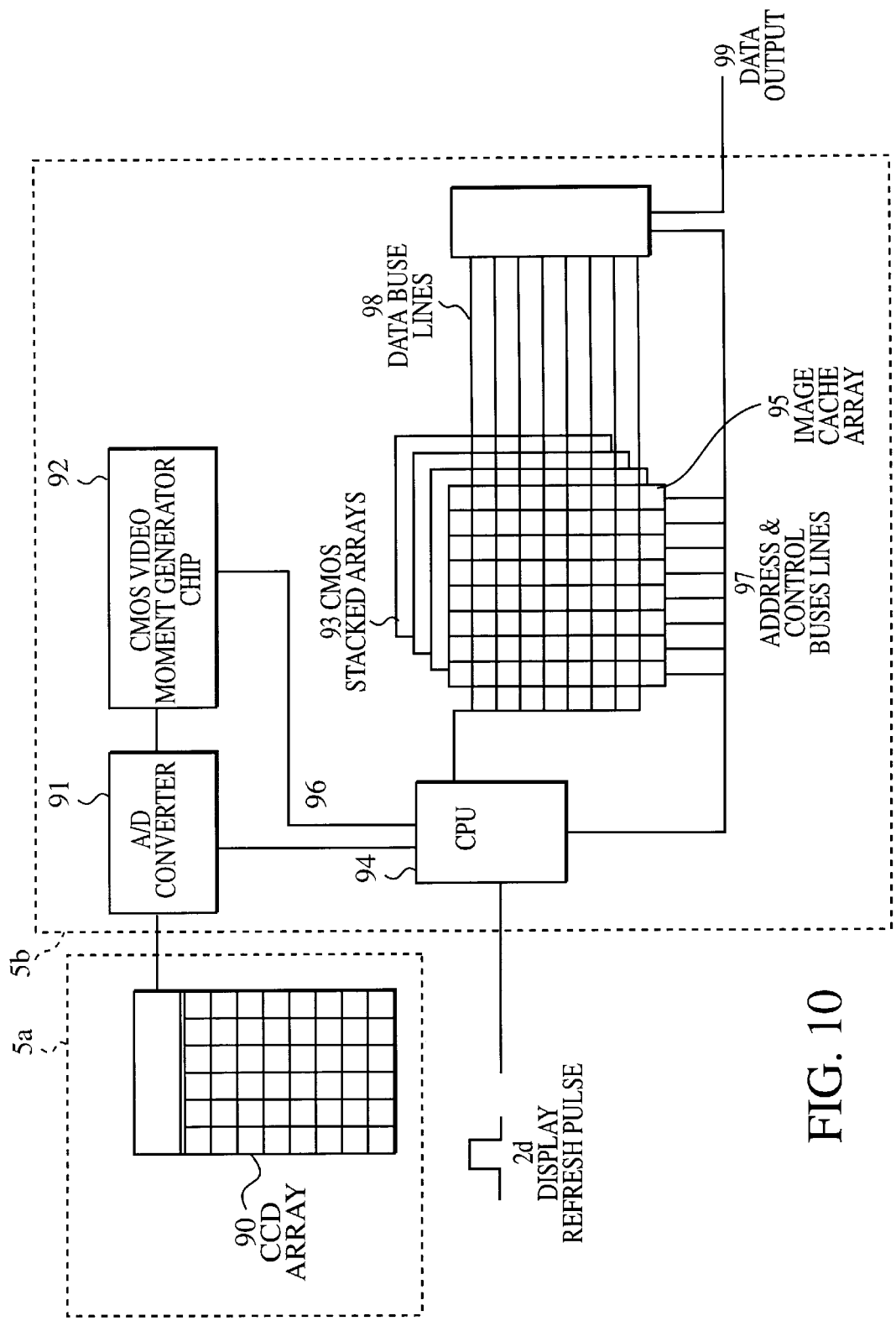
FIG. 10 is a schematic of the architecture for the image processor with a CCD array.

FIG. 10 shows the architecture of the image processor 5 and the interfacing of the image accumulator 5a to the image processing device 5b used to isolate image features. Here, the image accumulator 5a is a charge-coupled device (CCD) consisting of photosensitive Metal-Oxide-Silicon (MOS) capacitor elements arranged in a regular array 90. Referring back to FIG. 8, the array elements 66 receive analog light inputs from the outputs of the matched light regenerating elements 65 for the electronic integration of the eye's image over the display field refresh cycle of the display driver 2a. The feature isolation is performed on the accumulated image in 5a by the image processing device 5b upon receipt of the display field refresh pulse 2d from the display driver.

The image processing device 5b is embodied as a stack 93 of two dimensional very-large-scale-integrated (VLSI) circuit arrays made of CMOS wafers. Each array in the stack consists of identical digital processing elements which are matched between arrays by data bus lines 98 for image processing. The arrays are under the control of a central processing unit (CPU) 94 with common address and control bus lines 97. The CPU operates with a clock, instruction decoder, register, arithmetic and logic unit, and access to a memory cache with a stored program for stack control. The initial array of the stack is the digital memory cache 95 storing the digitized image. The remaining arrays of the stack consists of digital memory, comparators, counters, accumulators, and replicating elements. The stack functions by the CPU writing numerical values to the array elements and then operating the arrays en masse through the data and control bus lines.

The array elements of the stack 93 perform conventional digital functions: (1) the memory elements perform store, shift, invert, OR, and readout; (2) the accumulators store, add, and readout; (3) the replicating elements input, output, and perform stack control; (4) the counters count in and shift out; and (5) the comparators store reference values and output whether the input is greater, equal, or lower in value. The inputs to the stack are the digitized image cache 95 and the pupil image moments 96. The output 99 of the stack is a memory-mapped list of eye structure features and their image positions.

The accumulated image is transferred to the memory cache array 95 from the CCD array 90 upon receipt of the display field refresh pulse 2d. This is done by means of clocked serial bucket brigade downloaded to an analog-to-digital converter 91 with an analog input and a digital output. In the process, the output is read as a serial digital input by a very-large-scale-integrated (VLSI) circuit 92 on the data bus. The circuit is a video moment generator chip used to compute the image moments of the pupil and is made up of CMOS elements. The chip consists of a digital comparator for thresholding, and counters, shifters, adders, registers, and a programmable logic array (PLA). The digital comparator separates the serial digital input for the pupil image intensity from that for the iris and the sclera. The digital elements perform recursive moment computations on the resulting binary image under the control of the PLA. At the end of the serial transfer, the circuit outputs 96 the ellipsoidal moments of the pupil image: the centroid, the principal and minor axes, and deviations from these axes.

In preparation for feature processing the pupil image is isolated by the stack 93. The CPU 94 reads the pupil image moments from the video moment generator 92, following transfer of the digitized image to the digital memory cache 95. The CPU isolates the portion of the image containing the pupil by computing a template from the ellipsoidal moments and masking the image array cache. This is first done by writing "ones" into the elements of a memory array which match the pupil's template and "zeros" into the remaining. The CPU then uses an accumulator array to multiply the elements of the template array with the matched elements of the image array, and writing the products en masse to produce a masked memory array.

Figure 11:
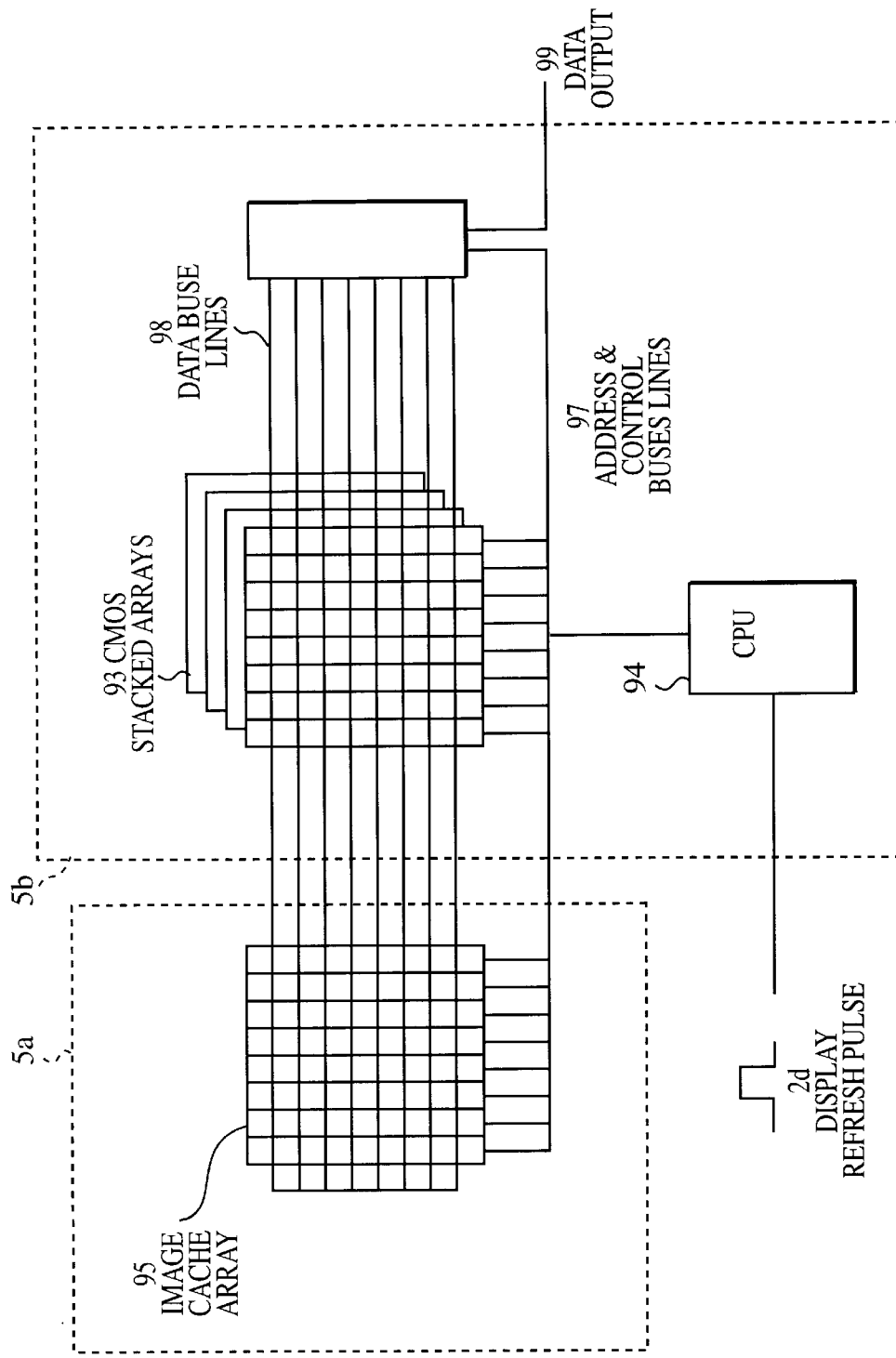
FIG. 11 is a schematic of the architecture for the image processor with a RAM cache array.

In the embodiment shown in FIG. 11, the image accumulator 5a is in the form of the random-access-memory (RAM) cache 95, where the cache is the initial array of the array stack 93 of the image processing device 5b. Referring to FIG. 9, the light regeneration elements of the image acquiring array 3d are replaced by analog-to-digital converters 65a with digital outputs to digital circuits 65b. The circuits are mapped one-to-one to the digital memory elements 66a of the cache, for the electronic integration of the eye's image over the display field refresh cycle of the display driver. In this embodiment, the CMOS video moment generator 92 of FIG. 10 is eliminated. Instead, the moments are computed using the array stack 93 under the CPU 94 control upon receipt of the display field refresh pulse 2d from the display driver. The stack performs an intensity thresholding and binary equalization of the digitized eye image held in the memory cache, and computes the ellipsoidal central moments from the thresholded pupil image.

Figure 12:
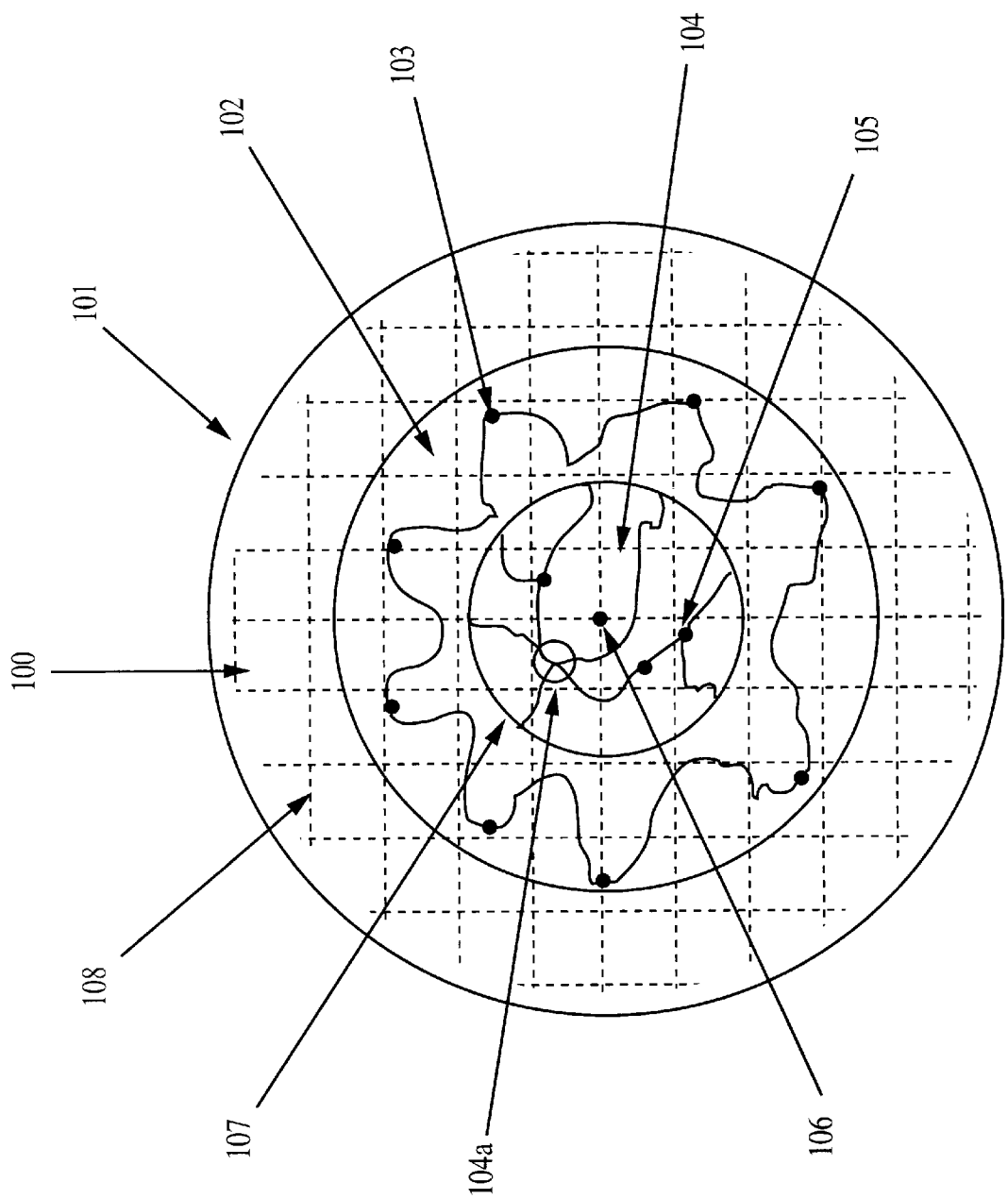
FIG. 12 shows the corneal reflection points and the internal structure points isolated from the image of the eye.

Following isolation of the pupil image, the stack 93 abstracts key image features shown in FIG. 12 for the human eye, such as the vascular capillary network 105 that overlays the retinal fundus 104. The vascular network radiates from the optic disk 104a at the back of the retina where the optic nerve (third cranial nerve) enters the eyeball. The portion of the retinal fundus that is visible in the image is determined by the diameter and orientation of the pupil 107. The pupil's diameter varies with the ambient lighting, from a fully open 7 millimeters for low light levels to 2 millimeters in bright light. For reference, the figure shows the sciera 101, the cornea 108, and the pupil centroid 106 as they appear in the eye's image. Shown also is the overlaid grid of corneal reflection points 100 that are not part of the image, but are computed from the pairing table 4a by a separate process.

The analysis of the vascular network is done through a series of consecutive image processing steps in which: (1) the pupil image is enhanced with histogram equalization, (2) the vascular network is enhanced with spatial gradient templates for edges and lines, (3) the network is segmented by binary thresholding, and (4) the junction points of the network segments are isolated as key features.

In a further embodiment, the stack isolates the cusps 103 of the pigmentary pattern on the sphincteral muscles of the iris 102, the opaque contractile diaphragm performed by the pupil. The sphincteral muscles contract or dilate the iris with changes in ambient light and accommodation. While the pattern changes with contraction, the general shape defined by the cusps remains invariant and unique to the individual. The stack isolates these key features through a series of consecutive processing steps, in which the first step is the isolation of the iris image from that of the eye. The remaining steps follow the vascular network analysis: (1) the iris image is enhanced with histogram equalization, (2) the outline of the pigmented portion of the iris is enhanced with spatial gradient templates for edges and lines, (3) the outline is segmented by binary thresholding, and (4) the cusp points of the outline are isolated. These image processing steps are now reviewed in greater detail.

The stack 93 isolates the iris image by intensity thresholding and binary equalization of the digitized eye image with removal of the pupil image. The intensity thresholding and binary equalization are performed by computing a threshold reference value with the histogram technique, and then using a replicator array to write the reference value to a comparator array. The gray scale intensities of the digital image memory cache 95 are then compared en masse, under control of the CPU 94. In this process, "zeros" are written to a memory array for intensities that are equal or less than the threshold, and "ones" for those that are greater.

The stack 93 computes the image moments from the thresholded memory array. The CPU 94 writes the moment coefficients to the elements of an accumulator array as a function of the coordinates of the element in the array and the moment-orders. The accumulator array repeatedly adds en masse the thresholded gray scale intensities according to the corresponding moment coefficients, and the accumulated sums are written to a memory array. The sums are accumulated as the contents of the memory array are shifted along the columns (rows). This continues as the contents are shifted along the row (column), following writing the summed column (row) results to the memory array. The CPU reads the array total as the value of the image moment. This action is repeated for all combinations of image moments of second order or less: (0,0), (1,0), (0,1), (2,0), (1,1), and (0,2). The ellipsoidal central moments, consisting of the centroid, principal and minor axes, and deviations from the axes of an elliptic representation, are then computed from these values. Finally, the image of interest is isolated by masking the image memory array with the thresholded memory array.

The stack computes an intensity histogram for an isolated image by first loading a comparator array with reference intensity levels, and then shifting the masked image array pass the comparator, while counting the occurrences of the levels. In detail, the CPU writes reference values into the columns (rows) of a comparator array with a replicator array, where the reference values are the same for each column (row) and the values are indexed from zero to the highest intensity level. The contents of the masked memory plane are then shifted along the rows (columns) of the array in a toroidal manner, while a counter array counts the comparator's "equal conditions". The counted values in the counter array are transferred to a memory array, and then summed in an accumulator as the memory array values are shifted along the columns (rows). Finally, the CPU reads the histogram distribution from the bottom row (column) of the accumulator.

The stack enhances the intensity contrast of the isolated image with histogram equalization. The CPU computes a histogram equalization mapping from the intensity histogram. Reference values are written into the columns (rows) of a comparator array with a replicator array, where the reference values are the same for each column (row) and the values are indexed from zero to the highest intensity level. The corresponding mapping function values for the histogram equalization are written to the elements of an accumulating array. The mapping function values are then written en masse to an enhanced memory array for the comparator's "equal condition" as the contents of the masked memory array and the enhanced memory array are shifted in step along the rows (columns) of the array in a toroidal manner.

The stack enhances the line-structure in the isolated image with a spatial gradient template. The CPU first zeros a destination accumulator array, and then performs a sequence of template matching processes on the enhanced image array. The template matching process first zeros a matching accumulator array, and then writes template weight values to an accumulator array. The enhanced image array is multiplied en masse by the template weights, and the products are added to the matching accumulator array. The enhanced image array is then shifted in turn left, right, down, up, and along each diagonal; and the above template weighting process is repeated for each shift. The absolute values of the contents for the template matching are then added to the destination accumulator array. This template matching operation is repeated for each template in the orthogonal set of line matching templates. Finally, the contents of the destination accumulator are written to a line-enhanced memory array.

The stack segments the enhanced line-structure (either retinal capillary network or pigmentary outline) by binary thresholding. An intensity histogram is first computed for the edge enhanced image, and a selected threshold value is then written as a reference value to the elements of a comparator array. The edge enhanced image is compared en masse to the threshold value. A "zero" or "one" is written to a memory array depending upon whether the intensity of an element of the image is less or equal to the threshold value, or if it is greater.

The stack isolates the junction points of the line segments by counting with an accumulator array, the number of neighboring pixels that are "one" for each "one"-pixel in the segmented image. For the junctions of the capillary network, the count is compared to a threshold of three with a comparator array; a "zero" is written to an isolation memory array for a count less than the threshold and "one" if equal or greater. For the sphincteral cusps on the iris, the count is compared to a threshold of two; a "one" is written to an isolation memory array for a count less than the threshold and "zero" if equal or greater.

The CPU stores the image coordinates of the junction points of the network segments in cache memory. This is done by reading the isolation array with the CPU as the elements are shifted by rows (columns) and columns (rows) until all elements are read, and storing the row and column addresses of those elements that are "one". Finally, at completion of the image feature isolation, the CPU outputs to a memory mapped area, the pupil moments and the image coordinates of the retinal network segment junctions and the iris-sphincteral cusps.

Figure 13:
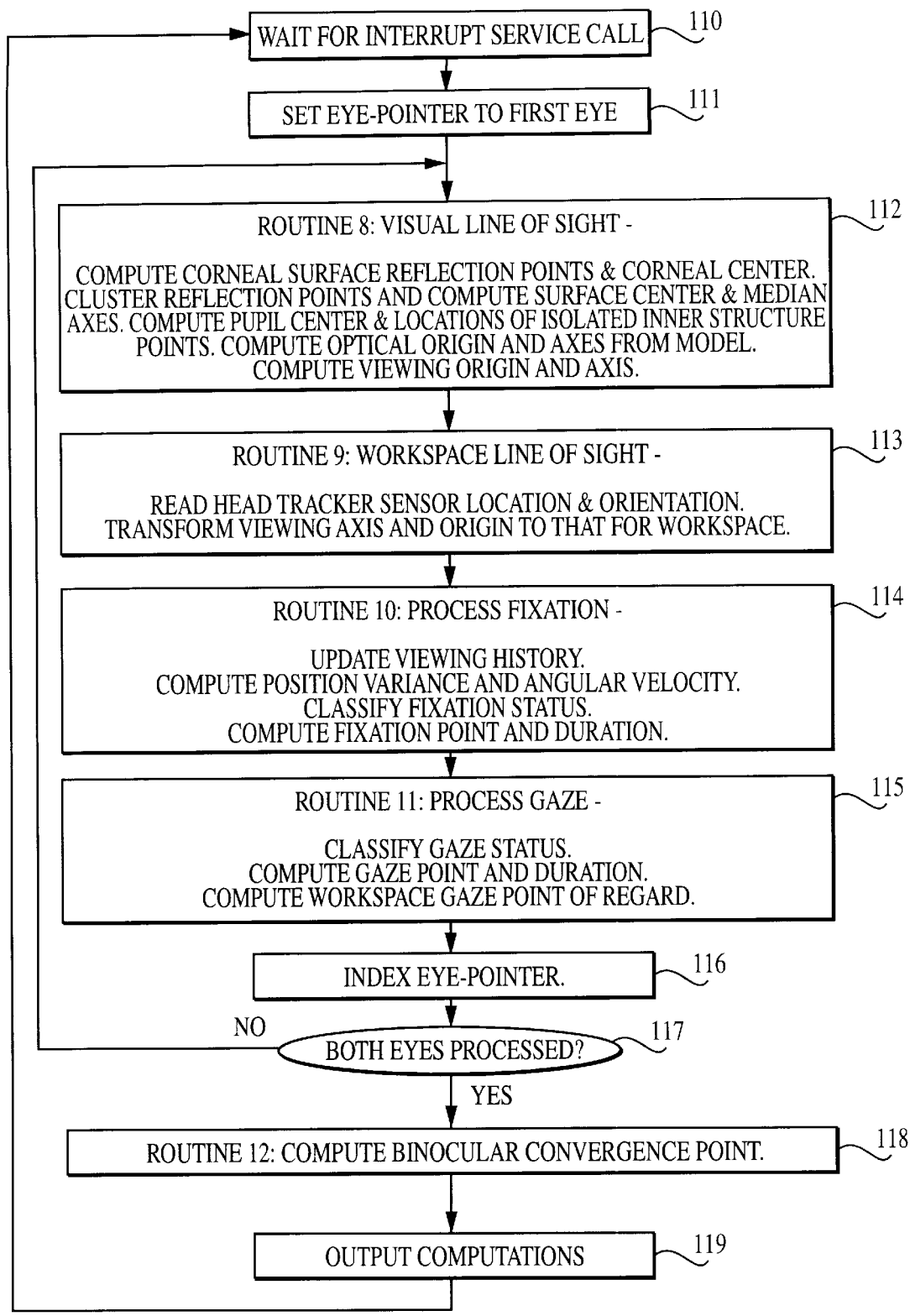
FIG. 13 is a flowchart of the digital computer routines used to process the light reflected from the user's eye during a display-field refresh cycle.

As flowcharted in FIG. 13, the digital computer 7 (FIG. 1) runs several processes which are released from hibernation upon receipt 110 of the display field refresh clock pulse 2d from the video display 2a. These are routines to compute 111 for each eye: (1) the visual line of sight 112 with routine 8, (2) the workspace line of sight 113 with routine 9, (3) the fixation status 114 with routine 10, and (4) the gaze point and status 115 with routine 11. The computer repeats the computations 116 for the other eye 117, and then computes the binocular convergence point 118 with routine 12, before outputting the computations 119 to a host computer. The routine 8 computes the visual line of sight relative to the optical device 2. The routine 9 reads the headset position and orientation from sensor 6 and transforms the visual line of sight to that for the real or virtual workspace which the user is viewing through the reflector/visor 36 of the optical device 2. The routine 10 maintains a running record of the line of sight and classifies the eye patterns as fixations, saccadic movements, or pursuit tracking. Finally, the routine 11 groups the eye fixations into cognitive meaningful gaze points and movements. Routine 12 uses the gaze points for both eyes to determine the binocular point of convergence for the dual eye system.

The routine 8 is essential for the functioning of the invention; the routine is based on a three dimensional model of the eye derived from the corneal light reflections and the eye's image data. As shown in FIG. 13 for item 112, the routine calls on a set of subroutines which compute in turn for the display refresh cycle: (1) the cornea's optical center and surface reflection points, (2) the smoothing of the reflection points, (3) the central point and median axes of the corneal surface, (4) the pupil's optical center, (5) the intraocular locations of the inner structure features, (6) the optical origin and axis, and (7) the viewing origin and axis. The subroutine for the corneal center makes use of the pairing table 4a and the geometry of optical device 2. Smoothing of the reflection points are required for computing the central point and median axes of the corneal surface. The subroutine for the pupil center uses the pupil centroid output of the processor 5b for the computations as well as the pairing table 4a. The subroutine for computing the inner structure locations uses the isolated feature output of the processor 5b and the pairing table 4a. The optical origin and axes are computed with a three dimensional model from the corneal and pupil centers, the corneal central point and median axes, the pupil moments, and the inner structure. Finally, the visual line of sight is computed from the optical origin and the optical and median axes.

The digital computer routine 8 computes the center of the corneal anterior surface in the coordinate system of the optical device 2 from the pairings listed for the sensor 2b and light source directions 2a in the memory table 4a. As part of this computation, the routine converts the pairing table to a mapping of the corneal surface locations of the reflection points and the corresponding corneal radii for the slightly ellipsoidal shape. The routine has in permanent memory the locations and orientations of the sensors 2b and sources 2a in the optical device 2 coordinate system referenced by the appropriate array addresses. The data file for the retinal scanning display contains the locations and directional cosines of the image light from the display in the coordinate system of the device 2 housing with the directional cosines determined by the display optics. Furthermore, the location and directional cosines for the sensors 2b are fixed in the display coordinate system by the sensor optics. These locations and directional cosines are computed prior to usage and fixed in permanent memory for the routine.

Figure 14:
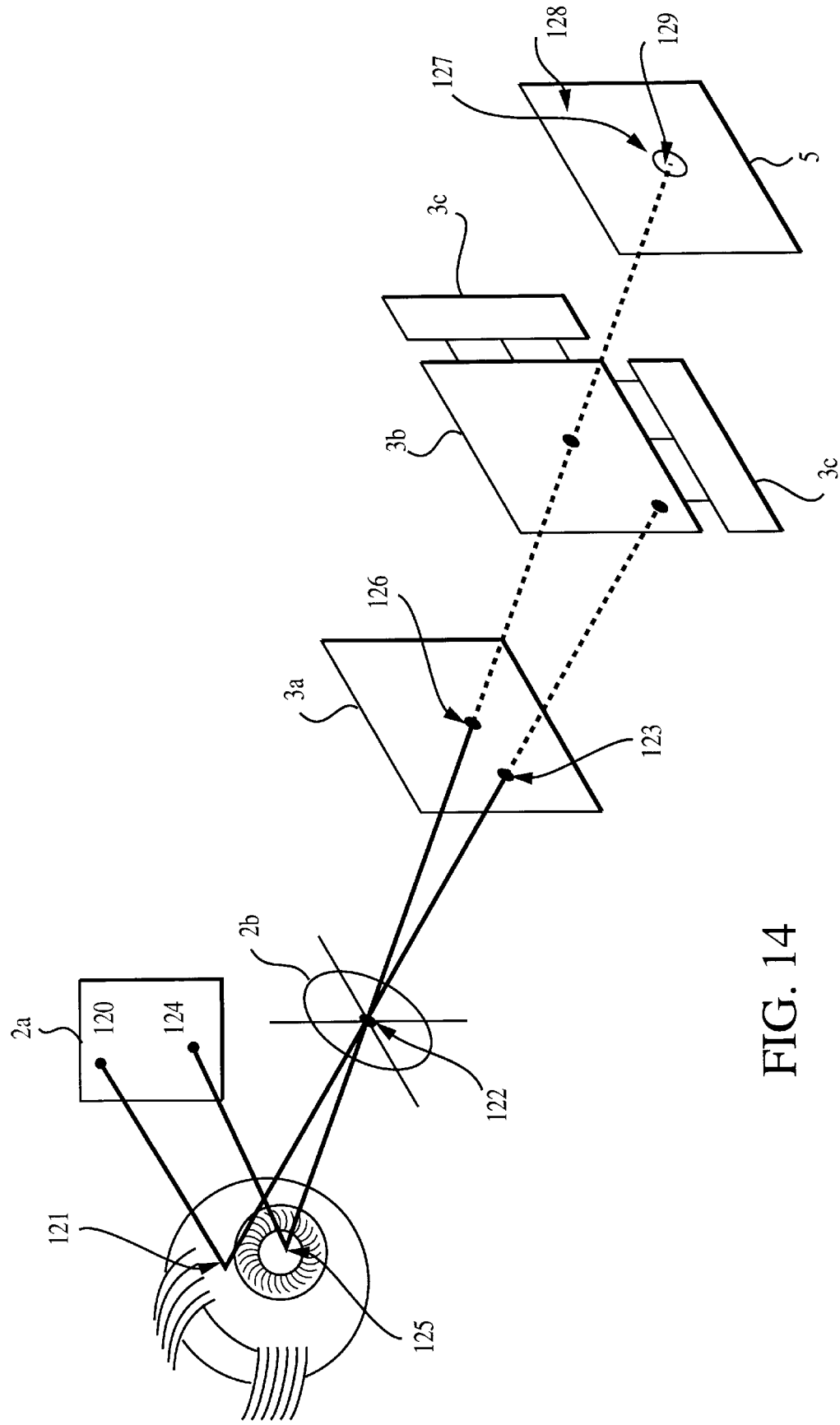
FIG. 14 is a schematic showing the processing of the light reflected from the user's eye during a display-field refresh cycle.

A set of five equations describes the relations between the center of the anterior spherical corneal surface, the direction of the display light source 2a, and the location and orientation of the sensor 2b paired at a corneal reflection point. These relations are shown in the geometry of FIG. 14 for the processing of the corneal reflection points. Three of the equations relate the reflection point 121 to the corneal center, the light source 120 location and direction, and the sensor orientation 122 and location 123. The application of Snell's law gives two more equations, one for the equality of the incident and reflection angles at the reflection point 121, and the other for the coplanar orientation of the source 120 ray, the reflection ray 122 reaching the sensor 123, and the corneal surface normal at the reflection point 121. Another equation is given by the fact that the corneal surface normal has unit magnitude.

Tabulated data from three pairings 4a of source lights to sensors are needed for an unique solution; regression analysis techniques are applicable with data from more than three pairings. The equations are solved using numerical analysis techniques. The output of the subroutine is the location of the corneal center in the coordinate system of the video device 2 housing and the corneal radius and reflection point coordinates for each pairing in the table 4a. The processor first solves for the directional cosines of the corneal surface normal at each paired reflection point using Snell's laws and the unit magnitude property; a unique solution is specified by the fact that the viewing direction is toward the display. The three equations relating the reflection point coordinates to the emitting source's location and direction and receiving sensor are then solved for the corneal center and the reflection points radii using the data from three or more pairings.

The tabulated mapping of the corneal surface locations of the reflection points for the paired light source directions and sensors and the associated corneal radii are used to determine key corneal features. The tabulated corneal radii are first smoothed by averaging over adjacent reflection points determined by a clustering algorithm based upon the proximity of angular separations about the corneal center. The table of smoothed radii are then searched for clusters with minimum, maximum, and average values. While the central 30-degrees of the corneal anterior surface is spherical in shape, the basilar surface is slightly astigmatic with two principal meridians perpendicular to each other. The corneal horizontal radius of curvature (normally 7.98 mm) is roughly equal to that of the optical center; however, the vertical radius is less (7.60 mm). Therefore, routine 8 first isolates minimum radii points that are separated by more than 30-degrees to define the vertical meridian. The surface point midway between the two minimum radii points defines the corneal surface center; the corneal radius is the distance between the corneal center and the surface center. Finally, routine 8 searches for radii points equal to corneal radius that are separated by more than 30-degrees, to define the horizontal meridian. Several checks on the mapping computations are made based on the expert knowledge of the cornea derived from the calibration process. First, the angular separations between the surface center and the reflection points for the maximum and minimum radii as measured from the corneal center should be fixed values normally greater than 15-degrees and less than 45-degrees. Further, the corneal radius should agree with that derived in calibration.

The pupil optical center and the locations of the inner structure features are computed by routine 8 using an ophthalmometric ray tracing technique. FIG. 14 shows the application of the technique to locate the pupil optical center in the coordinate system of the video device 2. The routine computes the locations of the pupil optical center from the corneal center, the pupil image center from 5b, and the source to sensor pairing table 4a. Here, the center 129 and major and minor axes of the pupil centroid 127 are shown in the coordinate system of the image plane 128 of the accumulator 5a. These values were stored along with the image coordinates of key features of the inner structure by the stack 93 in a memory mapped area accessible by routine 8. The pupil diameter is computed from the pupil image centroid major and minor axes.

In this process, the listing 4a of sensor to light source pairings is searched for a set of sensors which detect reflections surrounding and overlapping the apparent pupil image center. Because of the discrete arrangement of the source excitations, the image pupil center may lie between source reflection points. For this reason, the pairing table is searched for those reflection points which are nearest to the pupil image center. The corneal surface refraction point for the ray emitted from the optical pupil center is calculated by local surface fitting with numerical interpolation from the source to sensor pairings for the neighboring reflection points. As an example, in the figure a sensor 126 is shown detecting a reflection 125 which overlaps the apparent pupil image center 129. The light ray from the optical pupil center is transmitted through the eye and refracted by the cornea at the reflection point 125 to reach the image plane 128 of the accumulator 5a. The transmitted ray is coplanar to the incident and reflected light from the display source 125 paired to the sensor 126, and the refracted ray is parallel to the reflected light. The location of the reflection point 125 on the anterior surface of the cornea was computed from the locations and orientations of the source 124 and sensor 126. The directional cosines for the transmitted ray is computed from the corneal index of refraction and Snell's law relating the angle of incidence to the angle of refraction. In turn, the optical pupil center is computed from the corneal center and the distance between these centers, with the latter determined in calibration.

Figure 15:
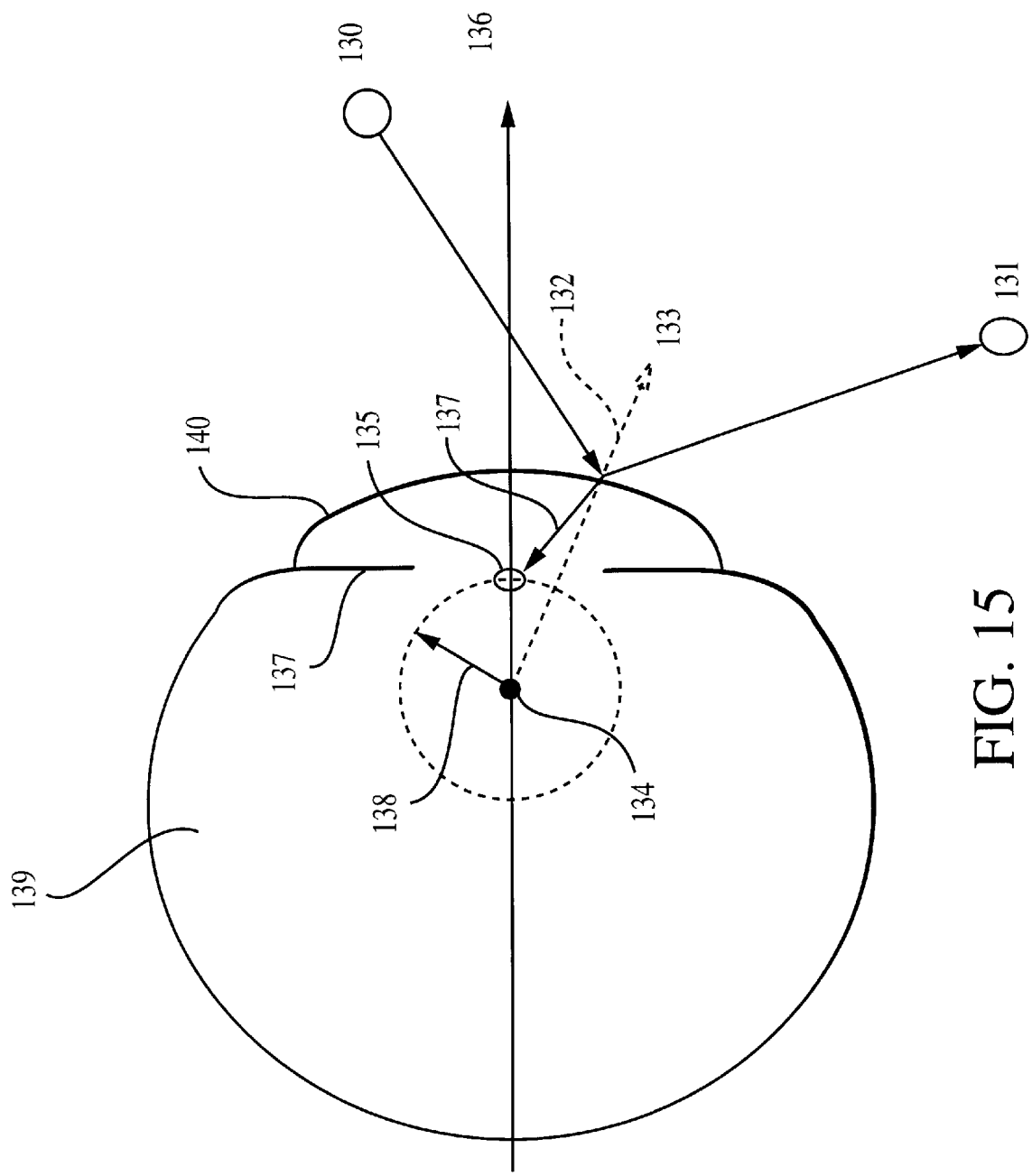
FIG. 15 is a schematic showing a cross-section of the eye with the use of ophthalmometric ray tracing to determine the pupil center.

FIG. 15 shows a crossectional view of the human eye with the geometry of the ophthalmometric ray tracing technique. Here the emitted ray from a light source 130 is reflected from the corneal surface 140 to a sensor 131 from the surface point 132. The emitted and reflected rays are coplanar with the surface normal 133 at the reflection point drawn from the corneal center 134, which is enclosed by the sclera 141. The refracted ray 137 back traced to the pupil center 135 defined by the iris 139, lies in this plane and intersects the optical axis 136 at a distance 138 from the corneal center. The separation distance 138 along the optical axis is determined in calibration, and conceptually defines a sphere centered on the corneal center. The pupil center 135 is the point at which the back traced refraction ray intersects the sphere. The value of the vector dot product formed from the directional cosines of the ray and the outer directed surface normal to the sphere, is negative at that point.

This technique of ophthalmometric ray tracing is further applied to determine the positions of the capillary junctions of the retinal fundus and the cusps of the sphincteral pattern on the iris. Again, the routine computes these locations using the memory mapped eye image locations from 5b and the source to sensor pairing table 4a. The listing 4a is searched for a set of sensors detecting nearest-neighbor reflections which surround and overlap the apparent image of the feature. The light ray from the feature is transmitted through the eye and refracted by the cornea at the surface point interpolated from the set of reflection points, to reach the image plane of the accumulator 5a. The location of the reflection points are computed from the locations and orientations of the corresponding sensors and paired source excitations. The directional cosines for the transmitted ray are computed from the corneal index of refraction and Snell's law relating the angle of incidence to the angle of refraction. In turn, the location of the feature is computed from the corneal center and the distance between the center and the feature as determined in calibration. The computations for the features of the retinal network include transmission through the crystalline lens and the internal vitreous body. The indexes of refraction for the aqueous humor and vitreous body are the same at 1.33; the index for the crystalline lens at 1.42 is nearly the same as that for the cornea at 1.38. The retinal scanning display shows a virtual reality image projected to infinity and the crystalline lens is assumed to be accommodated accordingly.

The routine computes the optical origin, and the optical and median axes by a best fit to a three dimensional model of the computed values. These are for the corneal optical and surface centers and the axes, the pupil optical center and orientation, and the optical locations of the key features for the capillary network of the retinal fundus and the sphincteral pattern of the iris. The corneal optic center, the surface center, and the median and normal axes are computed from the smoothed surface as above. The pupil orientation is computed from the image moments. The pupil optical center and the optical locations of the capillary network and the sphincteral pattern are computed using the ophthalmometric ray tracing method as above. The routine computes the center and directional cosines for the optical axis of the eye in the coordinate system of the video display 2. The roll of the eye is computed in an orthogonal set of coordinate axes that are perpendicular to the optical axis to complete the specification of the optical orientation.

The routine produces an accurate description of the optical axes and center in the display coordinate system for each display refresh cycle. However, the visual axis extends from the first Gaussian nodal point of the eye (normally near the center of curvature of the corneal anterior surface) and is commonly perpendicular to the cornea; it is generally directed 5 degrees inwards to the optical axis and 2 to 3 degrees upward. The visual axis is defined by an origin point in the optical axes coordinate system and three directional cosines determined in an initial calibration process. These parameters defining the visual axis are transformed into coordinates for the display coordinate system in routine 8 from the relations for the optical axes. The result is an accurate specification of the visual axis.

In some applications, the user may be viewing through the reflector/visor 36, an external real or virtual workspace which is independent of optical device 2; we may wish to know which elements of the visual workspace are being viewed. In this case, the visual line of sight computed by routine 8, must be transformed to that for the external workspace. This is accomplished by first locating the headset in the workspace. A tracking system 6 is used to measure the position and orientation of the headset 1 holding the video device 2. The tracking system consists of a source 6a, sensor 6b, and electronics processor 6c. The source is mounted in the user's workspace; the sensor is mounted on the headset. The system allows continual tracking of the six degrees of spatial freedom; the processing unit continually computes the position and orientation of the sensor relative to the source, and controls the transmission of the output data. Tracking systems are available employing different sources: infrared, ultrasonic, optical, and magnetic fields.

The computer routine 9 computes the user's viewing origin and direction in his visual workspace from the viewing point and axis given in the optical device 2 coordinates and the position and orientation of the headset as measured by the tracking system 6. The viewed point in the user's visual workspace is then computed using computer graphics concepts and a computer memory data base listing the objects and their locations in the user's workspace. The routine 9 computes the point of intersection of the viewing direction with each workspace surface facing the user from the surface normal and the location of a vertex. The routine checks to ensure that the intersection point is within the edges containing the surface. The viewed point is the contained intersection point closest to the user's eye.

The positions and orientations of the surfaces of the objects in the user's visual workspace are listed in a digital memory computer data file 9a by the directional cosines of their surface-normals and the coordinates of the vertices. The surfaces of the objects are described by a piece-wise net of planar segments for computational purposes. Note that the objects being viewed for a virtual workspace are those generated by the drawing file for the display driver of video display 2a; in this case, the digital memory computer data file 9a is defined by the virtual workspace used to set up the display driver. Similarly, the position coordinates and directional cosines of the orientation of the tracking system source 6a in the workspace are listed in the computer memory data file.

The computer routine 10 performs as an expert system, classifying the immediate visual state defined by the workspace viewing origin and direction, as fixation, saccade, pursuit or blink from an embedded expert knowledge base of these ocular states. The routine 10 detects saccades and predicts fixation end points, as well as separates saccades from pursuit eye tracking of moving targets, and eye blinks. The routine uses an automatic fixation and saccade classification scheme operated in conjunction with a saccadic end point predictor. The classification scheme is a combination of these two methods: the position variance method 10a and the velocity detection method 10b, operated as parallel processing channels. The end point predictor 10c is derived from a knowledge base on the relation between saccade peak velocity and amplitude of movement. The position variance method 10a is based on the expert knowledge that a fixation is characterized by relative immobility with low variance in eye movement, while a saccade is distinguished by rapid change (high variance) in position. In this method, the means and variances are computed for a sliding window of time samples in eye position. The variance of the windowed samples for a fixation is lower than an empirically determined threshold level. When a saccade occurs the variance rises, reaches a peak and then subsides toward the fixation level again. The initiation and termination of a saccade is automatically detected by comparing the position variance to the threshold level determined in an initial calibration process. Furthermore, curve fitting to the variance function is used to make predictions about the future variance values and therefore the time and location of the next fixation. The method has a time lag attributable to the width of the sampling window.

The velocity detection method 10b operates in parallel. In this method, the eye movement speed is computed from the windowed samples by first smoothing with a low-pass digital filter to remove noise, and then numerically differentiated. The computed speed is compared to an empirically determined threshold level separating saccadic movements from fixations. A speed above the threshold is classified as saccadic while that less than the threshold is classified as fixation. The position variance and velocity methods give similar results. These two methods are combined to obtain a more reliable saccade discriminator. The combined method can be based on either the agreement between the separate threshold outputs, or more elaborately, upon saccade state-probability estimates derived from the magnitudes of the position variance and speed measurements.

The saccadic end point predictor 10c is activated once a saccade has been detected. This method predicting the end point of the saccadic movement from the peak velocity, discriminates between saccades and pursuit tracking. The predictor is based on the expert knowledge that the eye-movement velocity function during a saccade is nearly symmetrical about a peak velocity located approximately half-way to the next fixation. In detail, the saccadic velocity function rises above the threshold detection level, accelerates to a peak velocity about half-way to the next fixation, and then decelerates below the threshold at the fixation point. Although it has been reported in the literature that a sine wave is a good fit for the velocity function, the function is in fact, more or less symmetrical depending upon the magnitude of the peak velocity. In actuality, the saccadal amplitude is related to the maximum velocity by an exponential function using curve fitting constants. A look up table contains empirically determined correction factors needed to adjust for the asymmetry in the velocity function. The correction factors are derived in the calibration process. Therefore, the processor by detecting the peak of the saccadal velocity, uses the relation to the saccadal amplitude to predict the termination time and location of the next fixation. A classification as saccadal movement that does not satisfy the end point predictor is reclassified as pursuit movement; these movements are less than 30 degrees per second. Blinks correspond to cases where no reflection points are detected due to obscuration of the cornea by the eyelid.

The user will tend to view a task related visual element with a sequence of fixations all in the same display area connected by small saccades. These fixations grouped together form a single gaze point of regard that more closely approximates the user's cognitive functioning. For this reason, the computer routine 11 groups the fixation data into task related visual gaze points. The routine uses a retrospective algorithm to determine the start, continuation, and termination of each gaze point as follows:

(1) A 100 millisecond sequence of eye fixations within 0.5 degrees of each other defines the start of a gaze point; the gaze point center is the mean of the eye fixations. The algorithm delay of 100 milliseconds is undetectable to the user.

(2) The gaze point is continued as long as eye fixations remain within one degree of the current gaze point center.

The gaze dwell time is the sum of the 100 millisecond start time and the current continuation time.

(3) A 50 millisecond sequence of eye positions that are beyond one degree of the current gaze point defines the termination of the present gaze. A blink up to 200 milliseconds is allowed without termination.

The routine 11 computes the gaze point as the visual viewing point of the eye as computed by routine 9 for pursuit tracking; initially pursuit tracking will consist of a saccade to acquire the target on the fovea followed by steady tracking. A rate varying target will be tracked with saccadic updating in tracking rate.

The routine 12 computes the convergence points of the left and right eye gaze directions for a dual eyetracker configuration. The convergence points are the points of closest approach between the two gaze lines; the line segment connecting the two lines at these points are perpendicular to both lines.

The invention has an embedded calibration process to determine the optical constants and parameters of a three dimensional model of the user's eye. A computer program calls for the sequential display of a series of cue markers for the user to look at. As each cue is displayed the program waits for the user's response and then collects the response data for that marker. The cue markers are placed in the visual scene so that the eye is in full view to the sensor array. This ensures that the optical axes may be derived from the source to sensor pairing table without reference to the eye's image. The invention is autocalibrating, and the user can quickly and accurately go through the calibration procedure.

By correlating eye gaze position with line of sight, the program computes the constants for a three dimensional eye model from the user's viewing response data. The corneal radius of curvature and the locations of the pupil optical center and the corneal center are computed. The junctions for the retinal capillary network and the cusps on the iris are isolated, and the program computes a three dimension model for the locations of these key features. Finally, the origin and directional cosines of the viewing direction are computed in the coordinate system of the optical axes.

In this process, the computer 7 of the invention has a digital output to the display driver of the calibration display, either that of the video display 2 or an additional display upon which a calibration marker may be displayed within the field of view of the viewer. A display prompting routine called by the calibration program sends a digital instruction to the display driver, causing a calibration marker to be displayed at a predetermined location within the visual field of the viewer. Following the display instruction, a delay routine is called which after a period of time long enough for the viewer to fixate the target, releases an interrupt service routine from hibernation. The interrupt service routine in response to the clocked display field refresh pulse output from the display driver 2a, calls in turn, upon the following routines.

A routine using a three dimensional model of corneal reflections, is called to compute the corneal center of each eye and the surface point locations of the reflections, from the source-to-sensor pairing table 4a and embedded memory tables of the geometry for the light source directions of the video driver 2a and the sensor array 2b. This is followed by a routine which smoothes the computed corneal reflections for each eye by clustering together surface points with nearly the same orientation relative to the corresponding corneal center. Another routine computes the optical origin and axis, and the median axes for the cornea of each eye from the corneal center and smoothed corneal reflection data. For the configuration with the calibration display unattached to the headset, a routine is called to read the position and orientation of the headset sensor 6. Finally, a routine is called to save this information along with the source-to-sensor pairing table, the image locations of the capillary junctions of the retinal fundus, and the locations of the sphincteral pattern cusps on the iris, for each calibration marker.

Once three calibration markers have been presented at separate locations, a routine is called to compute a set of constant parameters for each eye. These parameters relate the viewing origin and orientation to the optical origin and the optical and median axes, and are computed from the marker locations and when appropriate the headset positions and orientations. Another routine computes the corneal optic center to pupil center distance from the pupil image centroid; this is a constant parameter for each eye. The distances from the corneal center to the capillary junctions of the retinal fundus and the sphincteral pattern cusps on the iris for each eye, are also computed.

Following the display of the calibration marker at all locations, the calibration program computes the best estimate of the optical constants. These are done from the recordings for the calibration markers and the embedded memory tables of the geometry for the light source directions of the video display 2 and the sensor array 2b. Finally, a three dimensional model of the human eye is computed and saved in a memory file for reference by the computer program 8.

The invention is designed for use with head-mounted retinal scanning displays such as those developed for virtual reality, stereographic displays, monocular or binocular vision helmet mounted displays, and night vision goggles used in piloted helicopters, vehicles, and teleoperated robotics control stations. The accuracy of the invention is independent of shifts of the helmet on the user's head due to the ability to compute an exact eye model from the locations of the light sources and the sensors which are fixed by the helmet construction. The invention is used to provide measurements of information processing and workload which are needed for the proper functioning of a host computer controlling display formats. An example is the automated cueing of the user of an electronics intelligent pilot-vehicle interface display.

Figure 16:
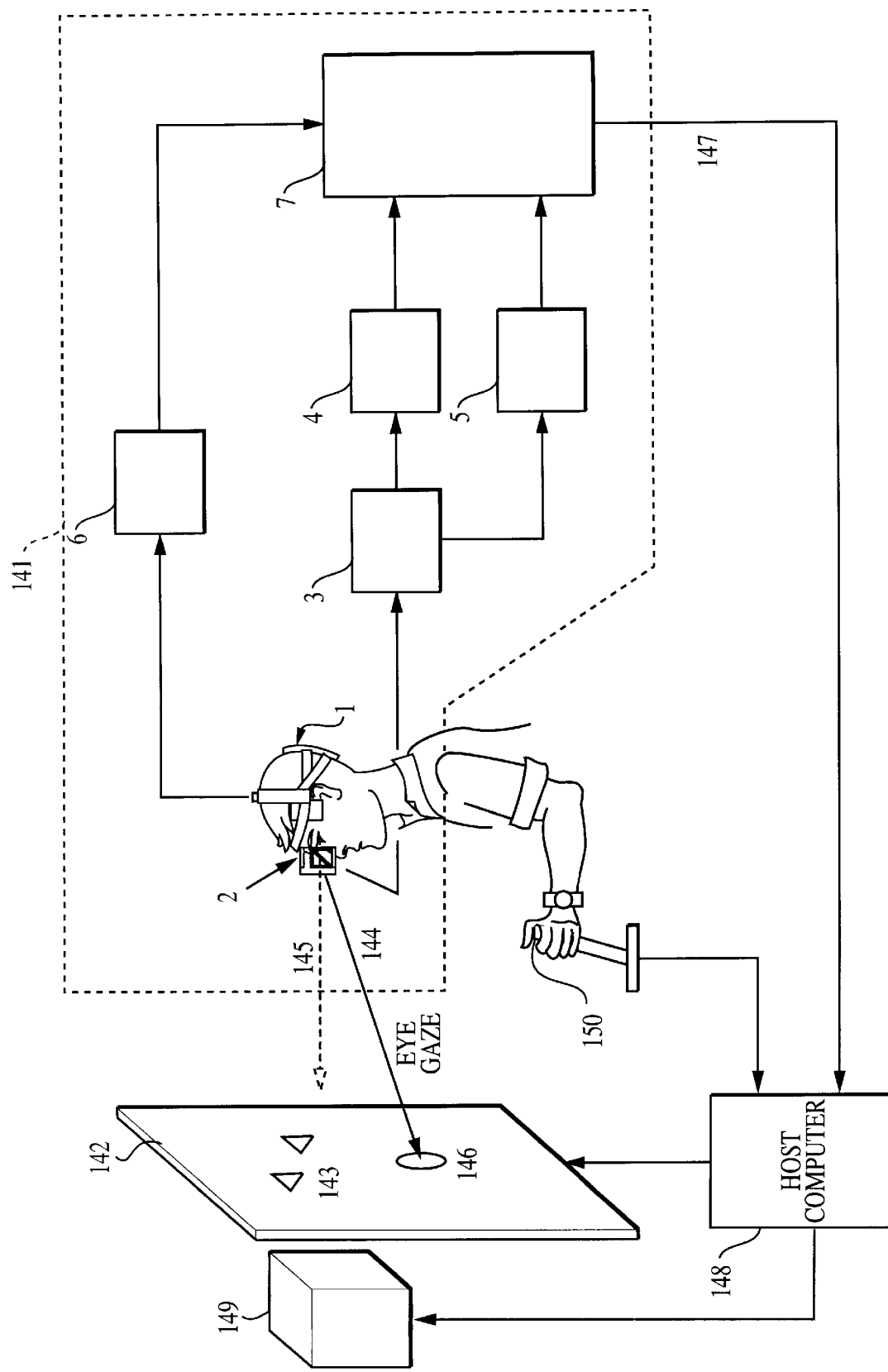
FIG. 16 is a schematic showing the application of the invention to the workstation.

FIG. 16 is a schematic showing an application of the invention to the workstation. The invention 141 by design serves as a peripheral to the host computer 148 which controls the display driver for task dedicated displays 142. The output 147 of the invention to the host computer in real time is: (1) the eye status flag, (2) the eye pupil size, (3) the gaze status flag, (4) the current gaze point location, (5) the gaze dwell time, (6) a task-interest flag, and (7) the head position and orientation from the output of routine 9. The eye status flag is the output of routine 10: fixation, saccade, pursuit, or blink. The gaze status flag indicates either the start of a gaze, continuation, or termination. The continuation flag and gaze dwell time are updated continually. The gaze location gives the point of regard 146 in both workspace coordinates and workspace surface by surface identifier and surface location. The gaze location is computed by routine 9 from the eye-gaze direction 144 and the head position and orientation 145. The routine has an initial 100 millisecond delay in detecting the start of a gaze and a 50 millisecond in detecting the end. The gaze dwell time is an indication of the user's cognitive task related interest in the visual element being studied. The dwell times tend statistically to be on the average longer for elements of interest.

The task-interest flag is reset to "non-interest" when the dwell time is less than a lower threshold value determined in calibration, usually about 150 milliseconds. However, the flag is set to "interest" when the dwell time exceeds an upper bound, usually about 250 milliseconds. The gaze status flag indicates a "saccade" during the large saccades that occur between gazes and "failure" when the processor fails to determine an eye position for more than 200 milliseconds. A further embodiment of the invention is the simultaneous tracking of both eyes with a dual display and sensor set. This supports the computation by computer routine 12 of the binocular convergence point in the user's three dimensional workspace for either real or virtual stereographic viewing. The convergence point is defined as the workspace point where the viewing axes are closest. In this case, the above output is made for both eyes separately along with the convergence point in the workspace coordinates.

The host computer upon receiving a set task-interest flag compares the gaze point location 146 to those listed for the visual display elements 143. Once a match is made, the host computer executes the appropriate task related routines updating the state of any controlled machinery 149 in the workspace and correspondingly, that of the visual display elements 143 as feedback to the user. However, in some cases, the selected decision may have critical implications for the task performance. An example is that of engaging hostile fire upon another vehicle in warfare. Note that the relation of gaze dwell time to task elements is a statistical process that may vary under stress as the task conditions change. For this reason, in the event of critical tasks, the host computer as an intermediate control step, will highlight the matched display element with a change in color, brightness, or shape as feedback to the user. The appropriate control routines are then implemented if the user executes a manual action in confirmation of the choice selection. The highlighting for element is dropped if the confirmation is not received within a preset time-out period, say several seconds. The manual confirmation action may be a button push 150 by the user or voice command via an automatic speech recognizer. Of course, the control routine executed along with the accompanying display update is determined by the display element selected and the host computer and associated display driver programs.

The eye status and pupil size are passed to the host computer for real-time human factors analysis; the gaze point and duration are all that is needed for specifying interest in a display element. However, there is evidence that pupil dilation and eye blinks are related to information processing stages and user's workload. These are factors which are important in controlling the rate and form of display element presentation by the host computer. For example, it has been shown that the pupil will dilate at the start of information processing reaching its maximum just before decision, and contract at the moment of decision making. The extent of the dilation is an inverse function of the intelligence of the viewer and direct function of the complexity of the problem to be solved. However, the pupil change is also a function of extraneous factors including ambient lighting and subject fatigue. For these reasons pupil dilation is a valid measure of the stages of information processing only in constant illumination displays for alert users.

Furthermore, blinks are reported to occur at transitions between stages of information processing. In particular, blinks appear to mark brief breaks that the brain takes at the end of each phase of a mental task, and in this way punctuate the sequence of mental events involved in acquiring and processing information. The occurrence of eye blinks may punctuate the appropriate moments to measure pupil dilation in information processing.

Another factor to consider is the level of workload which the user is experiencing. Eye blink rate has been shown to be non-linearity dependent on mental workload. Blink rate and duration are related to boredom, anxiety, and fatigue. Blink rate increases with boredom, anxiety, or other sources of physical or psychological stress. Fatigue increases blink duration. Attention to tasks demanding visual activity decreases the blink frequency. Head movements performed in conjunction with eye movements greater than 12-degrees, are an additional measure of workload.

Having thus shown and described what is at present considered to be the preferred embodiment of the present invention, it should be noted that the same has been made by way of illustration and not limitation. Accordingly, all modifications, alterations and changes coming within the spirit and scope of the present invention are herein meant to be included.

What is claimed is:

1. A device for measuring the ocular gaze point of regard and fixation duration, and the binocular convergence point of a viewer comprising:

an optical unit having a clocked raster-scan pulse output, a clocked display field refresh pulse output, and an optical output;

said optical unit connected to a headset having a head position and orientation sensor for displaying a visual image into the eyes of said viewer, said headset optically outputting the reflections from the cornea, pupil, and inner structure of said viewer's eyes;

an opto-electronic unit;

said opto-electronic unit having an input connected to said optical output of said optical unit, an input from said clocked raster scan pulse output of said optical unit, an analog light output of said viewer's eye image, and a digital output for transmitting a signal that electronically represents spatially the optical corneal reflection transmitted from said optical unit;

a double-buffered digital memory;

a digital processor;

said digital processor having an input from said clocked raster-scan pulse output of said optical unit, and input from said clocked display field refresh pulse output of said optical unit, and an input from said digital output of said opto-electronic unit to read said digital output from said opto-electronic unit on each clock-pulse and to write said digital output to said double-buffered digital memory;

an image processor;

said image processor having an input from said analog light output of said opto-electronic device, an input from said clocked display field refresh pulse output of said optical unit, and a memory mapped digital output comprising the image coordinates and principal axes for the pupil and inner structures of the eye of said viewer following each clocked field refresh pulse; and a digital computer;

said digital computer having an input from said output of said head position and orientation sensor, an input from said double-buffered digital memory, an input from said memory mapped digital output of said image processor, an input from said clocked display field refresh pulse output of said optical unit, and an output providing the computed gaze point of regard and fixation duration, and the binocular convergence point of said viewer following each said clocked display field refresh pulse;

said optical unit comprises a video display unit, a dielectric polarizer disposed in the path of light emanating from said video display to polarize said light, means for directing and focusing said polarized light onto the eyes of said viewer, a quarter-wave retarder plate, disposed in the path of said polarized light directed to and reflected from said viewers eyes, for rotating said polarized light one-half wavelength, a linear polarizer, disposed in the path of said polarized light reflected from the eyes of said viewer, for reflecting the polarized light in a direction away from the eyes of said viewer, and an optical lens, disposed in the path of said light reflecting off the eyes of said viewer after the light reflecting from said eyes has passed through said wave plate and reflected from said linear polarizing mirror, for optically filtering and focusing the corneal and inner reflections of said eyes in response to the illumination caused by said video display;

said video display comprises:
a retinal scanning display having a light emitting source activated so as to directly illuminate point-wise portions of the retina of said viewer with a modulated beam forming a diffraction-limited spot;
an electronic display driver where said driver excites said light emitting source in a sequential manner according to a specific display refresh order such that said display driver shifts the illuminating beam of said light emitting source to the next position in said order and concurrently modulates the output of said light emitting source for that position;
said display refresh order being in a raster scanning pattern forming an array of rows and columns such that a horizontal scanning action moves said beam to draw in turn a row of array pixel elements, and a vertical scanning action moves said beam to the start of the next row to repeat the drawing process; and
the refresh signal from said display driver for said array pixel elements being synchronized with the electrical output of said clocked raster-scan pulse from said video display to said opto-electronic device and said digital processor, and said display field refresh cycle for said display driver being synchronized with the output of said clocked display field refresh pulse from said video display to said image processor and said digital computer.

2. The device of claim 1 wherein said opto-electronic unit comprises:
a two-dimensional array of electronic opto-diode transistors having optical inputs from said optical output of said optical unit and having analog outputs;
an array of electronic comparators having analog inputs matched one-to-one to said analog outputs of said array of opto-diode transistors and having outputs wherein the output of each comparator is set when the output of the corresponding opto-diode transistor exceeds a threshold level and remains reset when it does not, wherein said threshold level comprises the specular reflection from said viewer's eye's cornea of the illumination from a display element of said video display unit;
an array of electronic bilateral switches having inputs matched one-to-one to the outputs of said array of comparators, wherein the state of each bilateral switch is determined by the output of the corresponding comparator such that the switch is closed for a set comparator and open for one reset;
an array of electronic inverters having inputs matched one-to-one to the outputs of said array of comparators and having an output which is the inverse of it input;
an array of two-way switches having analog outputs wherein one set of analog inputs are matched one-to-one to the outputs of said array of opto-diode transistors and wherein the other set of analog inputs are a signal ground with control signal inputs matched one-to-one to the outputs of said array of comparators and matching inverters;
an array of light-regenerating elements consisting of common collector transistors driving light emmiters having analog inputs matched one-to-one to the outputs of said array of two-way switches and having light emitting outputs;
said arrays interfaced so as to form independent parallel array points wherein each said point comprising the following elements in series:
a) an opto-diode transistor with the back-current output converted to a voltage output by an amplifier;
b) a threshold comparator where the voltage output of said amplifier is the input to said comparator and the threshold voltage for said comparator isset to that for the specular reflection from said cornea;
c) a bilateral switch where the voltage output of said comparator is the input to said bilateral switch and said switch is either closed or open as a function of the output of said comparator;
d) an inverter where the voltage output of said comparator is an input to said inverter;
e) a two-way selector switch having two inputs, one being the output of said amplifier and the other being a power ground, with control signals being the output of said comparator and said inverter;
f) a light regenerating element having input from said selector switch wherein said input is to the base voltage of a common collector transistor driving an emitter;
an electronic encoder having digital inputs from said array of bilateral switches and a digital output giving the array address of a set bilateral switch, wherein:
a) said array of bilateral switches are arranged such that the same side of the switches in the same array column are connected together to form an array row and the other side of the switches in the same array row are connected together to form an array column;
b) said array column are connected one-to-one to the address lines of a column encoder and the array rows are connected one-to-one to the address lines of a row encoder, the in-tap of one encoder is pulled high to the supply voltage, and the out-tap is read;
c) the address selector lines of the encoders are polled in a sequence for each row in turn for a column, and for each column in turn for all columns, by a decimal divider;
d) the clocked polling is stopped when the encoder out-tap is pulled high for a polled row and column for a bilateral switch with a set switch position;
an electronic latch which latches and holds the digital address output of said electronic encoder as output until reset by said clocked raster-scan pulse electrical output from said video display, where the reset is momentarily delayed to allow operation of said digital processor.

3. The device of claim 1, wherein said digital processor comprises:
means to read the digital output of the electronic latch for the encoded address of the set bilateral switches, and means to write the address to a double-buffered digital memory on each clocked raster-scan pulse outputted from said video display;
said double-buffered digital memory in the form of a list of light source positions and threshold activated optodiodes paired by the clocked raster scan pulse count, which functions as a source-to-sensor pairing table for the clocked display field refresh cycle; and said double-buffered digital memory buffered by the clocked display field refresh pulse outputted from said video display, and the resetting of the raster-scan pulse count to zero upon receipt of the display field refresh pulse.

4. The device of claim 1, wherein said image processor comprises:

a charge coupled device (CCD) having photosensitive Metal-OxideSilicon (MOS) capacitor elements arranged in a regular array, with analog light inputs from the outputs of said light regenerating elements, where said MOS capacitor elements are mapped one-to-one to the elements of the CCD with a relay lens array inserted between the stages to eliminate the beam spreading caused by diffraction, for the electronic integration of said viewer's eye's image over the display field refresh cycle of said video display;

a mechanism with a control line input, for the clocked serial transfer of the accumulated image in the CCD array to an analog to digital converter with a serial analog input and a digital output;

a very-large-scale-integrated (VLSI) video moment generator circuit made of CMOS elements having a digital comparator for thresholding, and digital counters, shifters, adders and registers under the control of a programmable logic array (PLA) for recursive moment computations, with a control line input, an input of the serial digital output from said clocked transfer mechanism, and digital outputs of the centroid, principal and minor axes and deviations from these axes, for an ellipsoidal image;

a stack of two dimensional VLSI circuit arrays made of CMOS wafers, with each array in the stack having identical digital processing elements which are matched between arrays by data bus lines for image processing under the control of a central processing unit (CPU), with common address and control bus lines, with an input of the serial digital output from said clocked transfer mechanism, an input of image moments from said moment generator circuit, and a mapped memory output of a list of inner eye elements and the coordinates of their image positions;

the first array of said stack being a digital memory cache which stores the digitized image received as input of the serial digital output from said clocked transfer mechanism;

the remaining arrays of said stack consisting of digital memory, comparators, counters, accumulators, and replicating elements; where
  a) the memory elements perform the functions of store, shift, invert, OR, and readout;
  b) the accumulators perform the functions of store, add, and readout;
  c) the replicating elements perform the functions of input, output, and stack control;
  d) the comparators store reference values and output whether the input is greater, equal, or lower in value; and
  e) the counters count in and shift out;

a central processing unit (CPU) with a clock, instruction decoder, register, arithmetic and logic unit, access to a memory cache with a stored program for stack control, access to the said common data, address and control bus lines for the stack, control outputs to said clocked transfer mechanism and to the moment generator circuit, and input from the clocked display field refresh pulse of said video display.

5. A method for processing an image of a human eye to compute the locations of points of interest on a line-structure contained within a predefined area comprising the steps of:

a) isolating the image area containing the line structure of interest by:
  (1) writing "ones" into a memory array for the array elements contained within a template defining the area and "zeros" into the remaining,
  (2) executing en masse the multiplication of the template array and the image array, and
  (3) writing the products into a masked memory array for matching elements;

b) computing a histogram for the isolated image by:
  (1) writing reference values into the columns (rows) of a comparator array, where the reference values are the same for each column (row) and the values are indexed from zero to the highest intensity level,
  (2) counting en masse the comparator's "equal conditions" with a counter array as the contents of the masked memory plane are shifted along the rows (columns) of the array in a toroidal manner,
  (3) transferring en masse the counted values in the counter array to a memory array,
  (4) summing en masse the counted values in an accumulator as the memory array values are shifted along the columns (rows), and
  (5) reading the bottom row (column) of the accumulator;

c) enhancing the intensity contrast of the isolated image with histogram equalization by:
  (1) computing a histogram equalization mapping from the intensity histogram,
  (2) writing reference values into the columns (rows) of a comparator array, where the reference values are the same for each column (row) and the values are indexed from zero to the highest intensity level,
  (3) writing the corresponding mapping function values to the elements of an accumulator array, and
  (4) writing the mapping function value to an enhanced memory array for the comparator's "equal condition" as the contents of the masked memory array and the enhanced memory array are shifted in step along the rows (columns) of the array in a toroidal manner;

d) enhancing the lines within the isolated image with a gradient template matching of the spatial contents for edges and lines by first zeroing a destination accumulator array, and then:
  (1) performing a template matching process using the enhanced image array and a matching accumulator array to accumulate the matched contents,
  (2) adding absolute values of the contents for the template matching to the destination accumulator array,
  (3) repeating the above template matching operation for each template in the orthogonal set of line matching templates, and
  (4) writing the contents of the destination accumulator to a line-enhanced memory array, where for each template, the template matching process is performed by first zeroing a matching accumulator array, and then: (a) writing template weight values to an accumulator array, (b) multiplying enhanced image array by template weights, (c) adding products to contents of matching accumulator array, (d) shifting enhanced image array in turn to left, right, down, up, and each diagonal, and repeating above template weighting process for each shift;
e) segmenting the line-structure of interest by binary thresholding, as follows:
  (1) computing the histogram for the edge enhanced image,
  (2) selecting a threshold value,
  (3) writing the threshold as a reference value to the elements of a comparator array, and
  (4) writing an "off" to a memory array if the intensity of an element of the edge enhanced image is less or equal to the comparator's threshold value and an "on" if it is greater;
f) isolating the points of the line-segments by:
  (1) counting the number with an accumulator array of neighboring pixels that are "on" for each on-pixel in the segmented image,
  (2) comparing the count to a threshold count with a comparator array, and
  (3) writing a non-count value to a memory array for a count less than the threshold, and a count value for equal or more; and
g) saving in cache memory the image coordinates of the points of the line segments, by reading the isolation array with the CPU as the elements are shifted by rows (columns) and columns (rows) until all elements are read, and storing the row and column addresses of those elements that are "on".

6. The device of claim 4, wherein elements of the said device are configured as follows:
a) replacement of the light regenerating array with an array of analog-to-digital converters interfaced to an array of digital read-add-write circuit elements, with the electrical analog inputs of the converters matched one-to-one to the outputs of the array of said two-way selector switches and with the digital outputs matched one-to-on of the pair of inputs of the said adders, where the said digital circuits add the values read from a mapped memory array to the outputs of the converters and write the sums to the memory array elements on receipt of the raster scan pulse from the video display;
b) replacement of the CCD array with a digital image memory cache, where the said digital read-add-write circuits are mapped one-to-one to the memory elements of the cache for the electronic integration of the eye's image over the clocked display field refresh cycle of the video display where the digital image memory cache is an array of the array stack; and
c) replacement of the moment generator circuit with a means for computing the image moments using the array stack under CPU control in accordance with a stored program, where the means, upon receipt of the display field refresh pulse from the visual display: (1) performs an intensity thresholding and binary equalization of the digitized eye image held in the said memory cache, and (2) computes the moments of the thresholded image; where
d) the intensity thresholding and binary equalization are performed by: (1) computing a threshold reference value with the histogram technique, (2) writing the reference value to a comparator array, (3) exercising the comparator array en masse, and (4) writing the compared values for the gray scale intensities of the digital image memory cache to a memory array as "zeros" for lesser or "ones" for greater values;
e) a moment is computed from the said thresholded memory array by: (1) the CPU computing and writing the image array moment coefficients to the elements of an accumulator array as a function of the coordinates of the element in the array and the moment orders, (2) the accumulator array repeatedly adding the thresholded gray scale intensities according to the corresponding moment coefficients, (3) the accumulator array writing the sums to a memory array, (4) the accumulator array adding the sums as the contents of the memory plane are shifted along the columns (rows) of the array, (5) the accumulator array adding the sums as the contents are shifted along the row (column), following writing the summed column (row) results to the memory plane, and (6) the CPU reading the total sum for the array as the moment; and
f) the CPU calling for the computation of the image moments of second order or less, and computing the central moments from these values, for the centroid, principal and minor axes, and deviations from the axes of an elliptic representation for the thresholded image.

7. A method for processing an image of the human eye to compute the moments of the pupil image and the locations of: (1) the capillary junctions of the retinal fundus, and (2) the cusps of the sphincteral pattern on the iris, comprising the steps of:
a) executing the following upon receipt by the CPU of the clocked display field refresh pulse of a video display;
b) computing the moments of the pupil image and an isolation template by:
  (1) initializing a clocked transfer mechanism for transfer of the accumulated image contained by a CCD to an analog-to-digital converter; initializing a moment generator circuit for analysis of the output of the same with the threshold of a comparator within the moment generator preset to pass only the pupil image; reading the serial digital output from a clocked analog-to-digital converter and writing the values to a digital image memory array cache of the stack; reading the output from the moment generator circuit upon acquisition of the digitized image from the clocked transfer mechanism; and computing a template from the ellipsoidal moments for isolating the pupil image from the digital image memory array cache;
c) determining the number of capillary junctions within the fundus of the image, by: isolating the pupil image with the said isolation template, enhancing the isolated pupil image by histogram equalization, enhancing the capillary network on the pupil fundus with application of spatial gradient templates for edges and lines, segmenting the network with binary thresholding, and isolating the junction points of the network segments with a count threshold of three, a non-count value of "off", and a count value of "on";
d) computing an isolation template for the iris by: calculating a threshold reference value with the histogram technique applied to the digitized eye image without the pupil image, intensity thresholding of the reduced image, and binary equalization of the same;
e) determining the number of cusps of the sphincteral pattern on the iris, by: isolating the iris image with the said isolation template, enhancing the isolated iris image by histogram equalization, enhancing the outline of the sphincteral pattern on the iris with application of spatial gradient templates for edges and lines, segmenting the outline with binary thresholding, and isolating the cusps of the pattern with a count threshold of two a non-count value of "on", and a count value of "off"; and f) outputting the pupil image moments and the image coordinates of the capillary junctions of the retinal fundus and the cusps of the sphincteral pattern on the iris, to a memory mapped area.

8. A method using an ophthalmomatric ray tracing approach for computing the intraocular location of an ocular feature from an eye image location a source-to-sensor pairing table the corneal optic center-to-feature distance, and the corneal center, comprising the steps of:

(a) finding a set of corneal reflection points which listed in a source-to-sensor pairing table are at or near the eye image location of the ocular feature so as to form a nearest-neighbor grid surrounding and overlapping the image of the feature;

(b) computing the optical locations of the corneal reflection points in the said nearest-neighbor set from the locations and orientations of the corresponding sensors and paired source excitations;

(c) computing the location of the corneal refraction point for the ocular feature with numerical interpolation by fitting a local surface to the set of neighboring reflection points;

(d) computing the surface normal for the said refraction point from the said location and the corneal optic center;

(e) computing the angle of incident for the light ray from the feature, from the location and surface normal of the said refraction point and the location of the corresponding sensor in the image plane of the accumulator;

(f) computing the directional cosines for the transmitted ray at the said refraction point from the corneal index of refraction and Snell's law relating the angle of incidence to the angle of refraction;

(g) tracing a ray from the said refraction point back to the ocular feature in the eye including transmission through the crystalline lens and the internal vitreous body;

(h) computing the intersection points of the ray with an imaginary sphere centered on the corneal optic center and having a radius equal to the intraocular distance between the center and the ocular feature as determined in calibration; and (i) determining the location of the feature from the said intersection points with the values of the vector dot products formed from the directional cosines of the back traced ray and the outer directed surface normals to the said imaginary sphere at the points of intersection from the corneal optic center.

9. A method for computing the gaze point of regard and fixation duration for each eye, and the binocular convergence point for both eyes of the viewer, using a digital computer program, comprising the steps of:

a) an interrupt service routine which in response to the clocked display field refresh pulse output from a video display, calls in turn, upon the following routines;

b) a routine for reading the position and orientation of a headset sensor;

c) a routine using a three dimensional model of corneal reflections, which computes the corneal center of each eye and the surface point locations of the reflections, from a source-to-sensor pairing table and embedded memory tables of the geometry's for light source locations and directions and a sensor array;

d) a routine which smooths the computed corneal reflections for each eye by clustering together surface points with nearly the same orientation relative to the corresponding corneal center, and computes the surface center, the surface normal at the center, and the median axes of the cornea from the smoothed surface;

e) a routine which computes the locations of the pupil optical center for each eye using an ophthalmomatric ray tracing approach and the corneal optic center to pupil center distance, from the corresponding said corneal center, a memory mapped pupil image center, and a source to sensor pairing table;

f) a routine which computes the locations of the capillary junctions of the retinal fundus and the cusps of the sphincteral pattern on the iris for each eye using an ophthalmomatric ray tracing approach and the corneal optic center distances, from the corresponding said corneal center, memory mapped eye image locations, and the source to sensor pairing table;

g) a routine which computes the optical origin, and the optical and median axes for each eye, by a best fit to a three dimensional model of the computed values for the corneal optic center, the corneal surface center and axes, the pupil optical center, the pupil orientation, the capillary network of the retinal fundus, and the sphincteral pattern of the iris;

h) a routine which computes the viewing origin and axis for each eye from the corresponding said optical origin and axis and the median axes;

j) a routine which converts the viewing origin and axis for each eye to that for the viewer's workspace from the said headset position and orientation sensor reading;

k) a routine which classifies the viewing status of each eye as saccadic, fixation, or pursuit from the corresponding immediate eye movement history;

l) a routine which classifies the gaze status of each eye by grouping local fixations, and computes the gaze point of regard in the viewer's workspace and fixation duration, from the corresponding viewing origin and axis, and an embedded memory table of the workspace geometry; and m) a routine to compute the binocular convergence point from the viewing origins and axes of both eyes for the viewer's workspace.

* * * * *